(12) United States Patent
Auernhammer et al.

(10) Patent No.: US 6,541,244 B1
(45) Date of Patent: Apr. 1, 2003

(54) SUPPRESSOR OF CYTOKINE SIGNALING (SOCS)-3 PROMOTER AND METHODS FOR ITS USE IN GENETIC THERAPY IN HUMANS

(75) Inventors: Christoph J. Auernhammer, Munchen-Pasing (DE); Shlomo Melmed, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 09/327,138

(22) Filed: Jun. 7, 1999

(51) Int. Cl.[7] .................. C12N 15/85; C12N 15/86; C07H 21/04

(52) U.S. Cl. .................. 435/320.1; 435/455; 435/456; 536/23.1; 536/23.5; 536/24.1

(58) Field of Search ................ 536/23.1, 23.5, 536/24.1; 514/44; 436/455, 320.1, 456

(56) References Cited

U.S. PATENT DOCUMENTS

| | | | |
|---|---|---|---|
| 4,959,313 A | 9/1990 | Taketo | 435/69.1 |
| 5,422,266 A * | 6/1995 | Cormier et al. | 435/252.3 |
| 5,532,143 A | 7/1996 | Grosveld | 435/69.1 |
| 5,547,940 A | 8/1996 | Nice | 514/21 |
| 5,610,053 A | 3/1997 | Chung | 435/461 |
| 5,648,235 A * | 7/1997 | Zurr et al. | 435/69.1 |
| 5,714,353 A * | 2/1998 | Pathak et al. | 435/91.42 |
| 5,824,838 A | 10/1998 | Melmed | 800/3 |
| 5,849,283 A | 12/1998 | Ciliberto | 424/85.2 |
| 5,863,529 A | 1/1999 | Rodriquez | 424/85.2 |
| 5,874,304 A * | 2/1999 | Zolotukhin et al. | 435/366 |

OTHER PUBLICATIONS

Verma et al., Gene therapy–promises,problems and prospects, Sep. 18, 1997, vol. 389, Nature, pp. 239–242.*
Rosenberg et al., Gene Therapist, Heal Thyself, Mar. 10, 200, vol. 287, Science.*
Ledley et al., Pharmaceutical Approach to Somatic Gene Therapy, Nov. 1996, Pharmaceutical Research, vol. 13, No. 11, pp. 1595–1614.*
XP–002095406, Minamoto, Seijiro et al., Cloning and Functional Analysis of New Members of STAT Induced STAT Inhibitor (SSI) Family: SSI–2 and SSI–3, *Biochemical and Biophysical Research Communications*, vol. 237, pp. 79–83 (1997).
XP–002150721, Heinrich, Peter C. et al., Review article, Interleukin–6–type cytokine signaling through the gp 130/Jak/STAT pathway[1], *Biochem J*, vol. 334, pp. 297–314 (1998).
XP–002150722, Auernhammer, C. J. et al., Autoregulation of pituitary corticotroph SOCS–3 expression: characterization of the murine SOCS–3 promoter, EMBL:AF117732, published *Proc. Natl. Acad. Sci. USA*, 96(12):6964–6969 (Jun. 8, 1999).

XP–002150723, Marra, M. et al., *The WashU–HHMI Mouse EST Project*, EMBL:MMAA24942 (Sep. 12, 1996).
XP–002150724, Marra M. et al., *The WashU–HHMI Mouse EST Project* EMBL:MM79831 (Apr. 14, 1993).
Auernhammer, C.J. et al., "Autoregulation of pituitary corticotroph SOCS–3 expression: Characterization of the murine SOCS–3 promoter", *Proc. Natl. Acad. Sci.*, vol. 96, pp. 6964–6969, Jun. 8, 1999.
Akita, S. et al., "Leukemia inhibitory factor (LIF) induces acute adrenocorticotrophic hormone (ACTH) secretion in fetal rhesus macaque primates: a novel dynamic test of pituitary function", *J. Clin. Endocrinol. Metab.*, 81(11): 4170–8, Nov. 1996, Abstract only.
Auernhammer, C.J. et al., "Leukemia inhibitory factor modulates interleukin–1beta–induced activation of the hypothalamo–pituitary–adrenal axis", *Endocrinology*, 139(5): 2201–8, May 1998.
Auernhammer, C.J. et al., "Pituitary corticotroph SOCS–3: novel intracellular regulation of leukemia–inhibitory factor–mediated proopiomelanocortin gene expression and adrenocorticotropin secretion", *Mol. Endocrinol.*, 12(7): 954–61, Jul. 1998.
Bousquet, C. et al., "A common pro–opiomelanocortin–binding element mediates leukemia inhibitory factor and corticotropin–releasing hormone transcriptional synergy",*J. Biol. Chem.*, 272(16): 10551–7, Apr. 18, 1997.
Chesnokova, V. et al., "Murine leukemia inhibitory factor gene disruption attenuates the hypothalamo–pituitary–adrenal axis stress response", *Endocrinology*, 139(5): 2209–16, May 1998.
Li, Q.L. et al., "Leukemia inhibitory factor (LIF) modulates pro–opiomelanocortin (POMC) gene regulation in stably transfected AtT–20 cells overexpressing LIF", *Endocrine*, 7(3): 325–30, Dec. 1997. Abstract only.
Ray, D.W. et al., "Leukemia inhibitory factor regulates proopiomelanocortin transcription", *Ann. N.Y. Acad. Sci.*, 840:162–73, May 1, 1998.

(List continued on next page.)

*Primary Examiner*—Scott D. Priebe
(74) *Attorney, Agent, or Firm*—Sidley Austin Brown & Wood LLP

(57) ABSTRACT

Disclosed is a nucleic acid construct comprising a murine SOCS-3 promoter sequence having SEQ. ID. NO.: 1, or a non-murine homologue thereof, or an operative fragment or derivative. The construct can also contain, operatively linked to the SOCS-3 promoter, a gene encoding any preselected protein, and optionally contains a reporter gene to facilitate detection and/or selection of successfully transfected cells. Also disclosed are a transgenic vertebrate cell containing the nucleic acid construct and transgenic non-human vertebrates comprising such cells. The nucleic acid construct is useful in methods of treating a growth retardation or growth acceleration disorder in a human subject and in a method of treating an autoimmune disease, immune disease, or inflammatory condition in a human subject. A kit for genetically modifying a vertebrate cell includes a polynucleotide comprising the murine SOCS-3 promoter sequence is also disclosed.

42 Claims, 6 Drawing Sheets

OTHER PUBLICATIONS

Ray, D.W., et al., "Leukemia inhibitory factor (LIF) stimulates proopiomelanocortin (POMC) expression in a corticotroph cell line. Role of STAT pathway.", *J. Clin. Invest.*, 97(8): 1852–9, Apr. 15, 1996.

Shimon, I. et al., "Cytokine–dependent gp130 receptor subunit regulates human fetal pituitary adrenocorticotropin hormone and growth hormone secretion", *J. Clin. Invest.*, 100(2): 357–63, Jul. 15, 1997.

Stefana, B. et al., "Leukemia inhibitory factor induces differentiation of pituitary corticotroph function: an immuno–neuroendocrine phenotypic switch", *Proc. Natl. Acad. Sci. USA*, 93(22): 12502–6, Oct. 29, 1996.

Wang, Z. et al., "Hypothalamic and pituitary leukemia inhibitory factor gene expression in vivo: a novel endotoxin–inducible neuro–endocrine interface", *Endocrinology*, 137(7): 2947–53, Jul. 1996.

Yano, H. et al., "Pituitary–directed leukemia inhibitory factor transgene causes Cushing's syndrome: neuro–immune–endocrine modulation of pituitary development", *Mol. Endocrinol.*, 12(11): 1708–20, Nov. 1998.

Adams, T.E. et al., "Growth hormone preferentially induces the rapid, transient expression of SOCS–3, a novel inhibitor of cytokine receptor signaling", *J. Biol. Chem.*, 273(3): 1285–7, Jan. 16, 1998, Abstract only.

Andrejko, K.M. et al., "Intrahepatic STAT–3 activation and acute phase gene expression predict outcome after CLP sepsis in the rat", *Am. J. Physiol.*, 275(6 Pt 1): G1423–9, Dec. 1998, Abstract only.

Banner, L.R. et al., "Leukemia inhibitory factor is an anti-–inflammatory and analgesic cytokine", *J. Neurosci.*, 18(14): 5456–62, Jul. 15, 1998, Abstract only.

Bjorbaek, C. et al., "Identification of SOCS–3 as a potential mediator of central leptin resistance", *Mol. Cell.*, 1(4): 619–25, Mar. 1998, Abstract only.

Boeuf, H. et al., "Leukemia inhibitory factor–dependent transcriptional activation in embryonic stem cells", *J. Cell Biol.*, 138(6): 1207–17, Sep. 22, 1997, Abstract only.

Ernst, M. et al., "Gp130–mediated signal transduction in embyronic stem cells involves activation of Jak and Ras/ mitogen–activated protein kinase pathways", *J. Biol. Chem.*, 271(47): 30136–43, Nov. 22, 1996, Abstract only.

Hagan, M.M. et al., "Role of the CNS Melanocortin System in the Response to Overfeeding", *J. Neurosci.*, 19(6): 2362–2367, Mar. 15, 1999, Abstract only.

Heinrich, P.C. et al., "Interleukin–6–type cytokine signalling through the gp130/Jak/STAT pathway", *Biochem. J.*, 334(Pt 2): 297–314, Sep. 1, 1998, Abstract only.

Hilton, D.J. et al., "Twenty proteins containing a C–terminal SOCS box form five structural classes", *Proc. Natl. Acad. Sci. USA*, 95(1): 114–9, Jan. 6, 1998, Abstract only.

Jenab, S. et al., "Testicular leukemia inhibitory factor (LIF) and LIF receptor mediate phosphorylation of signal transducers and activators of transcription (STAT)–3 and STAT–1 and induce c–fos transcription and activator protein–1 activation in rat Sertoli but not germ cells", *Endocrinology*, 139(4): 1883–90, Apr. 1998, Abstract only.

Kamura, T. et al., "The Elongin BC complex interacts with the conserved SOCS–box motif present in members of the SOCS, ras, WD–40 repeat, and ankyrin repeat families", *Genes Dev.*, 12(24): 3872–81, Dec. 15, 1998, Abstract only.

Katahira, M. et al., "Cytokine regulation of the rat proopiomelanocortin gene expression in AtT–20 cells", *Endocrinology*, 139(5): 2414–22, May 1998, Abstract only.

Kunisada, K. et al., "Activation of JAK–STAT and MAP kinases by leukemia inhibitory factor through gp130 in cardiac myocytes", *Circulation*, 94(10): 2626–32, Nov. 15, 1996, Abstract only.

Lecomte, M.J. et al., "Transcriptional activation of the mouse peripherin gene by leukemia inhibitory factor: involvement of STAT proteins", *J. Neurochem.*, 70(3): 971–82, Mar. 1998. Abstract only.

Marti, O. et al., "Activation of the hypothalamic–pituitary axis in adrenalectomised rats: potentiation by chronic stress", *Brain Res.*, 821(1): 1–7, Mar. 6, 1999, Abstract only.

Nicholson, S.E. et al., "Mutational analysis of the SOCS proteins suggest a dual domain requirement but distinct mechanisms for inhibition of LIF and IL–6 signal transduction", *EMBO. J.*, 18(2): 375–85, Jan. 15, 1999, Abstract only.

Nicholson, S.E. et al., "The SOCS proteins: a new family of negative regulators of signal transduction", *J. Leukoc. Biol.*, 63(6): 665–68, Jun. 1998, Abstract only.

Okabe, T. et al., "Nur77, a member of the steroid receptor superfamily, antagonizes negative feedback of ACTH synthesis and secretion by glucocorticoid in pituitary corticotrope cells", *J. Endocrinol.*, 156(1): 169–75, Jan. 1998, Abstract only.

Piekorz, R.P. et al., "Modulation of the activation status of Stat5a during LIF–induced differentiation of M1 myeloid leukemia cells", *Biochim. Biophys. Acta*, 1402(3): 313–23, Apr. 24, 1998, Abstract only.

Poulin, G. et al., "NeuroD1/beta2 contributes to cell–specific transcription of the proopiomelanocortin gene", *Mol. Cell Biol.*, 17(11): 6673–82, Nov. 1997, Abstract only.

Slominski, A. et al., "Expression of proopiomelanocortin (POMC)–derived melanocyte–stimulating hormone (MSH) and adrenocorticotropic hormone (ACTH) peptides in skin of basal cell carcinoma patients", *Human Pathol.*, 30(2): 208–15, Feb. 1999, Abstract only.

Song, M.M. et al., "The suppressor of cytokine signaling (SOCS) 1 and SOCS3 but not SOCS2 proteins inhibit interferon–mediated antiviral and antiproliferative activities", *J. Biol. Chem.*, 273(52): 35056–62, Dec. 25, 1998, Abstract only.

Starr, R. et al., "SOCS: suppressors of cytokine signalling", *Int. J. Biochem. Cell Biol.*, 30(10):1081–5, Oct. 1998, Abstract only.

Starr, R. et al., "A family of cytokine–inducible inhibitors of signalling", *Nature*, 387(6636): 917–21, Jun. 26, 1997, Abstract only.

Zhang, J.G. et al., The conserved SOCS box motif in suppressors of cytokine signaling binds to elongins B and C and may couple bound proteins to proteasomal degradation, *Proc. Natl. Acad. Sci. USA*, 96(5): 2071–2076, Mar. 2, 1999, Abstract only.

Galley, H.F. et al., "The immunoinflammatory cascade", *Br. J. Anaesth.*, 77: 11–16, 1996.

Murch, S.H. et al., "Local and Systemic Effects of Macrophage Cytokines in Intestinal Inflammation", *Nutritional and Gastrointestinal Disease*, 14: 780–783, 1998.

Veronesi, B. et al., "Particulate Matter Initiates Cytokine Release by Activation of Capsaicin and Acid Receptors in a Human Bronchial Epithelial Cell Line", *Toxicology and Applied Pharmacology*, 154: 106–115, 1999.

Grottrup–Wolfers, E. et al., "Elevated cell–associated levels of interleukin 1beta and interleukin 6 in inflamed mucosa of inflammatory bowel disease", *Eur. J. Clin. Invest.*, 26(2): 115–22, Feb. 1996, Abstract only.

Feldmann, M. et al., "Role of cytokines in rheumatoid arthritis", *Annu. Rev. Immunol.*, 14: 397–440, 1996, Abstract only.

Miossec, P., "Pro– and antiinflammatory cytokine balance in rheumatoid arthritis", *Clin. Exp. Rheumatol.*, 13 Suppl 12: S13–6, Sep.–Oct. 1995, Abstract only.

Reimund, J.M. et al., "Mucosal inflammatory cytokine production by intestinal biopsies in patients with ulcerative colitis and Crohn's disease", *J. Clin. Immunol.*, 16(3): 144–50, May 1996, Abstract only.

Chung, J.H. et al., "A 5' element of the chicken beta–globin domain serves as an insulator in human erythroid cells and protects against position effect in Drosophila", *Cell*, 74(3): 505–14, Aug. 13, 1993, Abstract only.

Chung, J.H. et al., "Characterization of the chicken beta–globin insulator", *Proc. Natl. Acad. Sci. USA*, 94(2): 575–80, Jan. 21, 1997.

* cited by examiner

SEQUENCE LISTING

<160> NUMBER OF SEQ ID NOS: 39

<210> SEQ ID NO 1
<211> LENGTH: 3940
<212> TYPE: DNA
<213> ORGANISM: Mus musculus
<220> FEATURE:
<221> NAME/KEY: promoter
<222> LOCATION: (-2907)...(1033)
<220> FEATURE:
<221> NAME/KEY: promoter

```
<222> LOCATION: (0)...(0)
<220> FEATURE:
<221> NAME/KEY: promoter
<222> LOCATION: (0)...(0)
<220> FEATURE:
<221> NAME/KEY: promoter
<222> LOCATION: (0)...(0)
<220> FEATURE:
<221> NAME/KEY: promoter
<222> LOCATION: (0)...(0)
<220> FEATURE:
<221> NAME/KEY: promoter
<222> LOCATION: (0)...(0)

<400> SEQUENCE: 1
gacgttccta aaagcatgca tgtcacccag cttacccacc catctcaggc cacagcagcc      60
tgagagagcg aagaacacc tgctggtcct gtcccacctc tcctcttcaa acagccccac     120
atcctccagt tttgctctgg gtggagctcc ctgctggccc tgcagaggga aggctctcct    180
aagcatcatc tatcagaacg tcttcaaaaa aaaaaaaaa aaaaaaaaag cctctccagc     240
caggctagct ctaacaccat ttcttcccct tccctctct caaattcact tatctttttt     300
tttttttttt tttttggatt tttgagacag ggtttctctg tatagccctg gttgtcctgg    360
aactcacttt gtacaccagc ctggcctcga actcagagat ccacctgcct ctgcctcctg    420
agtgctggga ttaaaggcgt gcgccaccac gcccggctaa attcacttat ctatttaatg    480
tatataggt ataggctgcc cttgaactca caaagatctg cttgctttgc ttctggaata     540
ctaaaggtgt gtgctaccat cacagggacc aagatttatt ttaattctgt atatgtgtgt    600
gtgtgtgtgt gtgtatgggg ggtgcacatg agtacagatt cccttggagg cctggggtgg    660
cttaggactg gggttacaac agttgtgacc catcctacat aggtcctggc accaacaccc    720
cccccccccc ccccgtcttc cagaagtgc agcaggtgtt cttaactgct gagccagcaa     780
tccagccct gacttccctc tcttacttaa gaagctatca cagtgtctca ctgggtcaca     840
atcatgacta gtccttgctc atggcccaca gcctcttccc cactgtgggt tttgccccgc    900
agctctgccg ccccagcgct gcacccgagg cctgacagag ccaggcacga agtcagggtt    960
tgtggaatgg atgaatgaac ttgactcgtg gcagagcatt gtaatttaca aagcactttc   1020
ccatccatta actccagggc tatttcctaa gagtcctccc tgtcctccac tgccctcggc   1080
tcagaggcat acggtcaagg cagtggctgg ggaacactcc ctgaatgaga tcaaggaggg   1140
cttgttcaca gagaaaggga gaatccattt ggggagcctg agagtgactc gaaggcaagg   1200
actgggcctc acctgtggga tctccatctg tgagcatccc ctcatcagac cagtgtgaga   1260
tattttaaat aaggcccta agcctcttga ctactggaat tgccagggc gggggacaga     1320
tgggcaccca tccctattta acagataaca agactgagtc cagagaggca gtgcacctgc   1380
cctggtctct cttagttcct cagcatcagt ggagcagatt ggacacagtg gccagaagg    1440
gaagcaggca gccctccctc ctagcccaag ctactctgtg tagtcagttt gccctcctac   1500
tggtgttaca agaagcctgt ggtatccaag agggcaggtc agaaagccca ctgagagcag   1560
acactgtgtg tcacttagct ggttctcagg tggctgccac ttcctgctgc ctgttgcaaa   1620
actcgacact aggcctttat agatactcac gtgaccagga gtaaacaacc tttcacctca   1680
atcacctgct cttatcaata ctccctctcc accccaccat cgggaaagtt cagacacctt   1740
aaaacgtaga ggcaagagag ggtccattct gacacctcag cgactttcag gcagtggctg   1800
```

```
aacccgttac aacgctctgt ggacagtcct cctagtcgac attccttctc aggtttgacc    1860
ctgtcctggg aagtgaggct tctctctctg ggttccccac tcctgttctt gaataaggag    1920
ccccacaacc tcttattctc tctatacaga gcctgggaaa cagcaaaact cggctcgcct    1980
acaagactcc agcgcgccct ctggtggact cgggggacga gcatgggatg agggtttctt    2040
tcctctagct cccccaccgc gccgagagta cctgggcgga cccacagttc gccacgcagg    2100
ttgggaggcc cagatgagtg ataaggtagt agttagctgc tcctcccacc ccactcccca    2160
aaggacatca gcacccacgt ctgtcaccga agaaccaggc aatgggcgga tgagctgagg    2220
ccaggtagct gcttctaagt cagtgtctcc tccacttctg gatctcacag cttcatcttt    2280
tggacctgtc tacaggtaaa tgtcgcgcat cccctcctc cacttcctag gtccccagtg    2340
ggctggtggc tgaatggtcc tacgtccctt ttggttggca cgggatgctt ggaactgtac    2400
atgaggacct cggggtggcc tgggtgcaga gggaggggag cgtccccgcg gggatcaaaa    2460
gaaagggaag gggtgccagg agggagcctc tcccggctgg cctcctagaa ctgcccgcgc    2520
gctcccatcg cgacgccccc gcctctgcca gaaaccagcc ttcttagaag ggagggggggg    2580
gaaagtgtga atgagaagtt gggggcggag cgcgcggggg aggggccgct gccaggaacg    2640
ctcggccaag gctggcgccg cgcccgccgg tcgggcagcc tcgcgccgcg ctttgtctcc    2700
ctctcggtga gtctcggcgg gtcctggagg ccccagctcc aagcccgccc tccgcagccc    2760
ctccctcgcc ctccgcgcac agcctttcag tgcagagtag tgactaaaca ttacaagaag    2820
accggccggg cagttccagg aatcgggggg cggggcgtac tggccgggta aatacccgcg    2880
cgcgcggcct ccgaggcggc tctaactctg actctacact cgcccgctcc tacgaccgct    2940
gtctctccgg gctcccggac gccccttcc cggcccagct ctccgtcgag gtccctcgcc    3000
cagtccttt gcctgattcg cccaggagtg cgcctcatcg gcccggggag cagcgaagcc    3060
agaggggcg cacgcacggg gagccccttt gtagacttca cggctgccaa catctgggcg    3120
cagcgcgagc cactgctggg cgccgcctcg cctcggggac cataggaggc gcagccccaa    3180
ggccggagat ttcgcttcgg gactaggtag aaggagggg cgcggtgtgg ggaagggtgg    3240
gggcatcggt ccagctcggg agcttttccc ggtttctcct cccttcccg ggtcattccc    3300
ggtagggagg ggacgaggca gggggcagag cggatgagaa ccgaagatcc ctgattcccg    3360
tcatactcag actggggccc tcgggtttct cctgtcccct ctctcacata tctcgggttt    3420
ggcaccccc tttttcgcc ctcgccactg aggacaccgg actgagaggc gccctgagcg    3480
tccctagggc tcttgtgtct ctccccatcc tggccgcgct cctggagacc caacttccac    3540
gcgcgagttt tctctgggcg tcctcctagg gcgggcaggg gaagagactg tctgggcttg    3600
gccggcagtg accgaggaca gtcgagttcc gcgaggtggc tgggcctgag acacggtcta    3660
aagcggggca aagggtgcc ccgggcgcta ggcggaggct ggagggccgg gcacgctgga    3720
gggttccggg cactcacgcg cctcacgctt tgctctctgc agctccccgg gatgcggtag    3780
cggccgctgt gcggaggccg cgaagcagct gcagccaccg ccgcgcagat ccacgctggc    3840
tccgtgcgcc atggtcaccc acagcaagtt tcccgccgcc gggatgagcc gccccctgga    3900
caccagcctg cgcctcaaga ccttcagctc caaaagcgag                          3940
```

<210> SEQ ID NO 2  
<211> LENGTH: 2863  
<212> TYPE: DNA  
<213> ORGANISM: Mus musculus  
<220> FEATURE:  
<221> NAME/KEY: promoter

<222> LOCATION: (-2759)...(104)

<400> SEQUENCE: 2

| | | | | | |
|---|---|---|---|---|---|
| ccctgctggc | cctgcagagg | gaaggctctc | ctaagcatca | tctatcagaa | cgtcttcaaa | 60
| aaaaaaaaaa | aaaaaaaaaa | agcctctcca | gccaggctag | ctctaacacc | atttcttccc | 120
| cttcccctct | ctcaaattca | cttatctttt | tttttttttt | tttttttgga | ttttttgagac | 180
| agggtttctc | tgtatagccc | tggttgtcct | ggaactcact | ttgtacacca | gcctggcctc | 240
| gaactcagag | atccacctgc | ctctgcctcc | tgagtgctgg | gattaaaggc | gtgcgccacc | 300
| acgcccggct | aaattcactt | atctatttaa | tgtatatagg | gtataggctg | cccttgaact | 360
| cacaaagatc | tgcttgcttt | gcttctggaa | tactaaaggt | gtgtgctacc | atcacaggga | 420
| ccaagattta | ttttaattct | gtatatgtgt | gtgtgtgtgt | gtgtgtatgg | ggggtgcaca | 480
| tgagtacaga | ttcccttgga | ggcctggggt | ggcttaggac | tggggttaca | acagttgtga | 540
| cccatcctac | ataggtcctg | gcaccaacac | cccccccccc | cccccccgtc | ttccagaagt | 600
| gcagcaggtg | ttcttaactg | ctgagccagc | aatccagccc | ctgacttccc | tctcttactt | 660
| aagaagctat | cacagtgtct | cactgggtca | caatcatgac | tagtccttgc | tcatggccca | 720
| cagcctcttc | cccactgtgg | gttttgcccc | gcagctctgc | cgccccagcg | ctgcacccga | 780
| ggcctgacag | agccaggcac | gaagtcaggg | tttgtggaat | ggatgaatga | acttgactcg | 840
| tggcagagca | ttgtaattta | caaagcactt | tcccatccat | taactccagg | gctatttcct | 900
| aagagtcctc | cctgtcctcc | actgccctcg | gctcagaggc | atacggtcaa | ggcagtggct | 960
| ggggaacact | ccctgaatga | gatcaaggag | ggcttgttca | cagagaaagg | gagaatccat | 1020
| ttggggagcc | tgagagtgac | tcgaaggcaa | ggactgggcc | tcacctgtgg | gatctccatc | 1080
| tgtgagcatc | cgctcatcag | accagtgtga | gatattttaa | ataaggcccc | taagcctctt | 1140
| gactactgga | attgccaggg | gcgggggaca | gatgggcacc | catccctatt | taacagataa | 1200
| caagactgag | tccagagagg | cagtgcacct | gccctggtct | ctcttagttc | ctcagcatca | 1260
| gtggagcaga | ttggacacag | tgggccagaa | gggaagcagg | cagccctccc | tcctagccca | 1320
| agctactctg | tgtagtcagt | ttgccctcct | actggtgtta | caagaagcct | gtggtatcca | 1380
| agagggcagg | tcagaaagcc | cactgagagc | agacactgtg | tgtcacttag | ctggttctca | 1440
| ggtggctgcc | acttcctgct | gcctgttgca | aaactcgaca | ctaggccttt | atagatactc | 1500
| acgtgaccag | gagtaaacaa | cctttcacct | caatcacctg | ctcttatcaa | tactccctct | 1560
| ccaccccacc | atcgggaaag | ttcagacacc | ttaaaacgta | gaggcaagag | agggtccatt | 1620
| ctgacacctc | agcgactttc | aggcagtggc | tgaacccgtt | acaacgctct | gtggacagtc | 1680
| ctcctagtcg | acattccttc | tcaggtttga | ccctgtcctg | ggaagtgagg | cttctctctc | 1740
| tgggttcccc | actcctgttc | ttgaataagg | agccccacaa | cctcttattc | tctctataca | 1800
| gagcctggga | aacagcaaaa | ctcggctcgc | ctacaagact | ccagcgcgcc | ctctggtgga | 1860
| ctcgggggac | gagcatggga | tgagggtttc | tttcctctag | ctcccccacc | gcgccgagag | 1920
| tacctgggcg | gacccacagt | tcgccacgca | ggttgggagg | cccagatgag | tgataaggta | 1980
| gtagttagct | gctcctccca | ccccactccc | caaaggacat | cagcacccac | gtctgtcacc | 2040
| gaagaaccag | gcaatgggcg | gatgagctga | ggccaggtag | ctgcttctaa | gtcagtgtct | 2100
| cctccacttc | tggatctcac | agcttcatct | tttggacctg | tctacaggta | aatgtcgcgc | 2160
| atccccctcc | tccacttcct | aggtcccag | tgggctggtg | gctgaatggt | cctacgtccc | 2220
| ttttggtttgg | cacgggatgc | ttggaactgt | acatgaggac | ctcggggtgg | cctgggtgca | 2280

-continued

```
gagggaggggg agcgtccccg cggggatcaa agaaaggga aggggtgcca ggagggagcc    2340
tctcccggct ggcctcctag aactgcccgc gcgctcccat cgcgacgccc ccgcctctgc    2400
cagaaaccag ccttcttaga agggaggggg gggaaagtgt gaatgagaag ttgggggcgg    2460
agcgcgcggg ggaggggccg ctgccaggaa cgctcggcca aggctggcgc cgcgcccgcc    2520
ggtcgggcag cctcgcgccg cgctttgtct ccctctcggt gagtctcggc gggtcctgga    2580
ggccccagct ccaagcccgc cctccgcagc ccctccctcg ccctccgcgc acagcctttc    2640
agtgcagagt agtgactaaa cattacaaga agaccggccg ggcagttcca ggaatcgggg    2700
ggcggggcgt actggccggg taaataccog cgcgcgcggc ctccgaggcg gctctaactc    2760
tgactctaca ctcgcccgct cctacgaccg ctgtctctcc gggctcccgg acgccccctt    2820
cccggcccag ctctccgtcg aggtccctcg cccaggtcct ttg                      2863
```

<210> SEQ ID NO 3
<211> LENGTH: 3686
<212> TYPE: DNA
<213> ORGANISM: Mus musculus
<220> FEATURE:
<221> NAME/KEY: promoter
<222> LOCATION: (-2759)...(927)

<400> SEQUENCE: 3

```
ccctgctggc cctgcagagg gaaggctctc ctaagcatca tctatcagaa cgtcttcaaa     60
aaaaaaaaaa aaaaaaaaaa agcctctcca gccaggctag ctctaacacc atttcttccc    120
cttcccctct ctcaaattca cttatctttt tttttttttt tttttttgga tttttgagac    180
agggtttctc tgtatagccc tggttgtcct ggaactcact ttgtacacca gcctggcctc    240
gaactcagag atccacctgc ctctgcctcc tgagtgctgg gattaaaggc gtgcgccacc    300
acgcccggct aaattcactt atctatttaa tgtatatagg gtataggctg cccttgaact    360
cacaaagatc tgcttgcttt gcttctggaa tactaaaggt gtgtgctacc atcacaggga    420
ccaagattta ttttaattct gtatatgtgt gtgtgtgtgt gtgtgtatgg ggggtgcaca    480
tgagtacaga ttcccttgga ggcctgggt ggcttaggac tggggttaca acagttgtga    540
cccatcctac ataggtcctg gcaccaacac ccccccccc ccccccgtc ttccagaagt     600 gcagcaggtg ttcttaactg ctgagccagc aatccagccc ctgacttccc tctcttactt    660
aagaagctat cacagtgtct cactgggtca caatcatgac tagtccttgc tcatggccca    720
cagcctcttc cccactgtgg gttttgcccc gcagctctgc cgccccagcg ctgcacccga    780
ggcctgacag agccaggcac gaagtcaggg tttgtggaat ggatgaatga acttgactcg    840
tggcagagca ttgtaatta caaagcactt tcccatccat taactccagg gctatttcct    900
aagagtcctc cctgtcctcc actgccctcg gctcagaggc atacggtcaa ggcagtggct    960
ggggaacact ccctgaatga gatcaaggag ggcttgttca cagagaaagg gagaatccat   1020
ttggggagcc tgagagtgac tcgaaggcaa ggactgggcc tcacctgtgg gatctccatc   1080
tgtgagcatc cgctcatcag accagtgtga gatatttaa ataaggcccc taagcctctt   1140
gactactgga attgccaggg gcgggggaca gatgggcacc catccctatt taacagataa   1200
caagactgag tccagagagg cagtgcacct gccctggtct ctcttagttc ctcagcatca   1260
gtggagcaga ttggacacag tgggccagaa gggaagcagg cagccctccc tcctagccca   1320
agctactctg tgtagtcagt ttgccctcct actggtgtta caagaagcct gtggtatcca   1380
agagggcagg tcagaaagcc cactgagagc agacactgtg tgtcacttag ctggttctca   1440
```

-continued

```
ggtggctgcc acttcctgct gcctgttgca aaactcgaca ctaggccttt atagatactc    1500
acgtgaccag gagtaaacaa cctttcacct caatcacctg ctcttatcaa tactccctct    1560
ccaccccacc atcgggaaag ttcagacacc ttaaaacgta gaggcaagag agggtccatt    1620
ctgacacctc agcgactttc aggcagtggc tgaacccgtt acaacgctct gtggacagtc    1680
ctcctagtcg acattccttc tcaggtttga ccctgtcctg ggaagtgagg cttctctctc    1740
tgggttcccc actcctgttc ttgaataagg agccccacaa cctcttattc tctctataca    1800
gagcctggga aacagcaaaa ctcggctcgc ctacaagact ccagcgcgcc ctctggtgga    1860
ctcgggggac gagcatggga tgagggtttc tttcctctag ctcccccacc gcgccgagag    1920
tacctgggcg gacccacagt tcgccacgca ggttgggagg cccagatgag tgataaggta    1980
gtagttagct gctcctccca ccccactccc caaaggacat cagcacccac gtctgtcacc    2040
gaagaaccag gcaatgggcg gatgagctga ggccaggtag ctgcttctaa gtcagtgtct    2100
cctccacttc tggatctcac agcttcatct tttggacctg tctacaggta aatgtcgcgc    2160
atccccctcc tccacttcct aggtccccag tgggctggtg gctgaatggt cctacgtccc    2220
ttttggttgg cacgggatgc ttggaactgt acatgaggac ctcggggtgg cctgggtgca    2280
gagggagggg agcgtccccg cggggatcaa agaaaggga aggggtgcca ggagggagcc    2340
tctcccggct ggcctcctag aactgcccgc gcgctcccat cgcgacgccc ccgcctctgc    2400
cagaaaccag ccttcttaga agggagggggg gggaaagtgt gaatgagaag ttgggggcgg    2460
agcgcgcggg ggaggggccg ctgccaggaa cgctcggcca aggctggcgc cgcgcccgcc    2520
ggtcgggcag cctcgcgccg cgctttgtct ccctctcggt gagtctcggc gggtcctgga    2580
ggccccagct ccaagcccgc cctccgcagc ccctccctcg ccctccgcgc acagcctttc    2640
agtgcagagt agtgactaaa cattacaaga agaccggccg ggcagttcca ggaatcgggg    2700
ggcggggcgt actggccggg taaatacccg cgcgcgcggc ctccgaggcg gctctaactc    2760
tgactctaca ctcgcccgct cctacgaccg ctgtctctcc gggctcccgg acgccccttt    2820
cccggcccag ctctccgtcg aggtccctcg cccaggtcct ttgcctgatt cgcccaggag    2880
tgcgcctcat cggccggggg agcagcgaag ccagagggg cgcacgcacg gggagccccct    2940 ttgtagactt cacggctgcc aacatctggg cgcagcgcga gccactgctg ggcgccgcct    3000
cgcctcgggg accataggag gcgcagcccc aaggccggag atttcgcttc gggactaggt    3060
aggaaggagg ggcgcggtgt ggggaagggt gggggcatcg gtccagctcg ggagcttttc    3120
ccggtttctc ctcccttcc cgggtcattc ccggtaggga ggggacgagg caggggcag    3180 agcggatgag aaccgaagat ccctgattcc cgtcatactc agactggggc cctcgggttt    3240
ctcctgtccc ctctctcaca tatctcgggt ttggcacccc cctttttcg ccctcgccac    3300 tgaggacacc ggactgagag gcgccctgag cgtccctagg gctcttgtgt ctctccccat    3360
cctggccgcg ctcctggaga cccaacttcc acgcgcgagt tttctctggg cgtcctccta    3420
gggcgggcag gggaagagac tgtctgggt tggccggcag tgaccgagga cagtcgagtt    3480
ccgcgaggtg gctgggcctg agacacggtc taaagcgggg caaagggtg ccccgggcgc    3540 taggcggagc ctggagggcc gggcacgctg gagggttccg ggcactcacg cgcctcacgc    3600
tttgctctct gcagctcccc gggatgcggt agcggccgct gtgcggaggc gcgaagcag    3660 ctgcagccac cgccgcgcag atccac                                        3686
```

<210> SEQ ID NO 4

<211> LENGTH: 2791
<212> TYPE: DNA
<213> ORGANISM: Mus musculus
<220> FEATURE:
<221> NAME/KEY: promoter
<222> LOCATION: (-1864)...(927)

<400> SEQUENCE: 4

| | | | | | |
|---|---|---|---|---|---|
| ttcctaagag | tcctccctgt | cctccactgc | cctcggctca | gaggcatacg | gtcaaggcag | 60 |
| tggctgggga | acactccctg | aatgagatca | aggagggctt | gttcacagag | aaagggagaa | 120 |
| tccatttggg | gagcctgaga | gtgactcgaa | ggcaaggact | gggcctcacc | tgtgggatct | 180 |
| ccatctgtga | gcatccgctc | atcagaccag | tgtgagatat | tttaaataag | gcccctaagc | 240 |
| ctcttgacta | ctggaattgc | caggggcggg | ggacagatgg | gcaccatcc | ctatttaaca | 300 |
| gataacaaga | ctgagtccag | agaggcagtg | cacctgccct | ggtctctctt | agttcctcag | 360 |
| catcagtgga | gcagattgga | cacagtgggc | cagaagggaa | gcaggcagcc | ctccctccta | 420 |
| gcccaagcta | ctctgtgtag | tcagtttgcc | ctcctactgg | tgttacaaga | agcctgtggt | 480 |
| atccaagagg | gcaggtcaga | aagcccactg | agagcagaca | ctgtgtgtca | cttagctggt | 540 |
| tctcaggtgg | ctgccacttc | ctgctgcctg | ttgcaaaact | cgacactagg | cctttataga | 600 |
| tactcacgtg | accaggagta | acaacctttt | cacctcaatc | acctgctctt | atcaatactc | 660 |
| cctctccacc | ccaccatcgg | gaaagttcag | acaccttaaa | acgtagaggc | aagagagggt | 720 |
| ccattctgac | acctcagcga | ctttcaggca | gtggctgaac | ccgttacaac | gctctgtgga | 780 |
| cagtcctcct | agtcgacatt | ccttctcagg | tttgaccctg | tcctgggaag | tgaggcttct | 840 |
| ctctctgggt | tccccactcc | tgttcttgaa | taaggagccc | cacaacctct | tattctctct | 900 |
| atacagagcc | tgggaaacag | caaaactcgg | ctcgcctaca | agactccagc | gcgccctctg | 960 |
| gtggactcgg | gggacgagca | tgggatgagg | gtttctttcc | tctagctccc | ccaccgcgcc | 1020 |
| gagagtacct | gggcggaccc | acagttcgcc | acgcaggttg | ggaggcccag | atgagtgata | 1080 |
| aggtagtagt | tagctgctcc | tcccacccca | ctccccaaag | gacatcagca | cccacgtctg | 1140 |
| tcaccgaaga | accaggcaat | gggcggatga | gctgaggcca | ggtagctgct | tctaagtcag | 1200 |
| tgtctcctcc | acttctggat | ctcacagctt | catcttttgg | acctgtctac | aggtaaatgt | 1260 |
| cgcgcatccc | cctcctccac | ttcctaggtc | cccagtgggc | tggtggctga | atggtcctac | 1320 |
| gtccctttg | gttggcacgg | gatgcttgga | actgtacatg | aggacctcgg | ggtggcctgg | 1380 |
| gtgcagaggg | agggagcgt | ccccgcgggg | atcaaaagaa | agggaagggg | tgccaggagg | 1440 |
| gagcctctcc | cggctggcct | cctagaactg | cccgcgcgct | cccatcgcga | cgccccgcc | 1500 |
| tctgccagaa | accagccttc | ttagaaggga | ggggggggaa | agtgtgaatg | agaagttggg | 1560 |
| ggcggagcgc | gcggggagg | ggccgctgcc | aggaacgctc | ggccaaggct | ggcgccgcgc | 1620 |
| ccgccggtcg | ggcagcctcg | cgccgcgctt | tgtctccctc | tcggtgagtc | tcggcgggtc | 1680 |
| ctggaggccc | cagctccaag | cccgccctcc | gcagccctc | cctcgccctc | cgcgcacagc | 1740 |
| ctttcagtgc | agagtagtga | ctaaacatta | caagaagacc | ggccgggcag | ttccaggaat | 1800 |
| cgggggggcgg | ggcgtactgg | ccgggtaaat | acccgcgcgc | gcggcctccg | aggcggctct | 1860 |
| aactctgact | ctacactcgc | ccgctcctac | gaccgctgtc | tctccgggct | cccggacgcc | 1920 |
| cccttcccgg | cccagctctc | cgtcgaggtc | cctcgcccag | gtcctttgcc | tgattcgccc | 1980 |
| aggagtgcgc | ctcatcggcc | cggggagcag | cgaagccaga | gggggcgcac | gcacggggag | 2040 |
| cccctttgta | gacttcacgg | ctgccaacat | ctgggcgcag | cgcgagccac | tgctgggcgc | 2100 |

-continued

| | |
|---|---|
| cgcctcgcct cggggaccat aggaggcgca gccccaaggc cggagatttc gcttcgggac | 2160 |
| taggtaggaa ggaggggcgc ggtgtgggga agggtgggggg catcggtcca gctcgggagc | 2220 |
| tttccccggt ttctcctccc cttcccgggt cattcccgt agggagggga cgaggcaggg | 2280 |
| ggcagagcgg atgagaaccg aagatccctg attcccgtca tactcagact ggggccctcg | 2340 |
| ggtttctcct gtcccctctc tcacatatct cgggtttggc acccccttt tttcgccctc | 2400 |
| gccactgagg acaccggact gagaggcgcc ctgagcgtcc ctagggctct tgtgtctctc | 2460 |
| cccatcctgg ccgcgctcct ggagacccaa cttccacgcg cgagttttct ctgggcgtcc | 2520 |
| tcctagggcg ggcaggggaa gagactgtct ggggttggcc ggcagtgacc gaggacagtc | 2580 |
| gagttccgcg aggtggctgg gcctgagaca cggtctaaag cggggcaaag gggtgccccg | 2640 |
| ggcgctaggc ggaggctgga gggccgggca cgctggaggg ttccgggcac tcacgcgcct | 2700 |
| cacgctttgc tctctgcagc tccccgggat gcggtagcgg ccgctgtgcg gaggccgcga | 2760 |
| agcagctgca gccaccgccg cgcagatcca c | 2791 |

<210> SEQ ID NO 5
<211> LENGTH: 1803
<212> TYPE: DNA
<213> ORGANISM: Mus musculus
<220> FEATURE:
<221> NAME/KEY: promoter
<222> LOCATION: (-857)...(927)

<400> SEQUENCE: 5

| | |
|---|---|
| gggtttctttt cctctagctc ccccaccgcg ccgagagtac ctgggcggac ccacagttcg | 60 |
| ccacgcaggt tgggaggccc agatgagtga taagtagta gttagctgct cctcccaccc | 120 |
| cactccccaa aggacatcag cacccacgtc tgtcaccgaa gaaccaggca atgggcggat | 180 |
| gagctgaggc caggtagctg cttctaagtc agtgtctcct ccacttctgg atctcacagc | 240 |
| ttcatctttt ggacctgtct acaggtaaat gtcgcgcatc cccctcctcc acttcctagg | 300 |
| tccccagtgg gctggtggct gaatggtcct acgtcccttt tggttggcac gggatgcttg | 360 |
| gaactgtaca tgaggacctc ggggtggcct gggtgcagag ggagggagc gtccccgcgg | 420 |
| ggatcaaaag aaagggaagg ggtgccagga gggagcctct cccggctggc ctcctagaac | 480 |
| tgcccgcgcg ctcccatcgc gacgcccccg cctctgccag aaaccagcct tcttagaagg | 540 |
| gagggggggg aaagtgtgaa tgagaagttg ggggcggagc gcgcggggga ggggccgctg | 600 |
| ccaggaacgc tcggccaagg ctggcgccgc gcccgccggt cgggcagcct cgcgccgcgc | 660 |
| tttgtctccc tctcggtgag tctcggcggg tcctggaggc cccagctcca agcccgccct | 720 |
| ccgcagcccc tccctcgccc tccgcgcaca gcctttcagt gcagagtagt gactaaacat | 780 |
| tacaagaaga ccggccgggc agttccagga atcggggggc ggggcgtact ggccgggtaa | 840 |
| ataccccgcgc gcgcggcctc cgaggcggct ctaactctga ctctacactc gcccgctcct | 900 |
| acgaccgctg tctctccggg ctcccggacg ccccttccc ggcccagctc tccgtcgagg | 960 |
| tccctcgccc aggtcctttg cctgattcgc ccaggagtgc gcctcatcgg cccggggagc | 1020 |
| agcgaagcca gagggggcgc acgcacgggg agccccttttg tagacttcac ggctgccaac | 1080 |
| atctgggcg agcgcgagcc actgctgggc gccgcctcgc ctcggggacc ataggaggcg | 1140 |
| cagccccaag gccggagatt tcgcttcggg actaggtagg aaggaggggc gcggtgtggg | 1200 |
| gaagggtggg gcatcggtc cagctcggga gcttttcccg gttctcctc cccttcccgg | 1260 |
| gtcattcccg gtagggaggg gacgaggcag ggggcagagc ggatgagaac cgaagatccc | 1320 |

| | |
|---|---|
| tgattcccgt catactcaga ctggggccct cgggtttctc ctgtccctc tctcacatat | 1380 |
| ctcgggtttg gcacccccct tttttcgccc tcgccactga ggacaccgga ctgagaggcg | 1440 |
| ccctgagcgt ccctagggct cttgtgtctc tccccatcct ggccgcgctc ctggagaccc | 1500 |
| aacttccacg cgcgagtttt ctctgggcgt cctcctaggg cgggcagggg aagagactgt | 1560 |
| ctggggttgg ccggcagtga ccgaggacag tcgagttccg cgaggtggct gggcctgaga | 1620 |
| cacggtctaa agcggggcaa aggggtgccc cgggcgctag gcggaggctg gagggccggg | 1680 |
| cacgctggag ggttccgggc actcacgcgc ctcacgcttt gctctctgca gctccccggg | 1740 |
| atgcggtagc ggccgctgtg cggaggccgc gaagcagctg cagccaccgc cgcgcagatc | 1800 |
| cac | 1803 |

<210> SEQ ID NO 6
<211> LENGTH: 990
<212> TYPE: DNA
<213> ORGANISM: Mus musculus
<220> FEATURE:
<221> NAME/KEY: promoter
<222> LOCATION: (-63)...(927)

<400> SEQUENCE: 6

| | |
|---|---|
| gggggggcggg gcgtactggc cgggtaaata cccgcgcgcg cggcctccga ggcggctcta | 60 |
| actctgactc tacactcgcc cgctcctacg accgctgtct ctccgggctc ccggacgccc | 120 |
| ccttcccggc ccagctctcc gtcgaggtcc ctcgcccagg tcctttgcct gattcgccca | 180 |
| ggagtgcgcc tcatcggccc ggggagcagc gaagccagag ggggcgcacg cacggggagc | 240 |
| cccttgtag acttcacggc tgccaacatc tgggcgcagc gcgagccact gctgggcgcc | 300 |
| gcctcgcctc ggggaccata ggaggcgcag ccccaaggcc ggagatttcg cttcgggact | 360 |
| aggtaggaag gaggggcgcg gtgtggggaa ggtgggggc atcggtccag ctcgggagct | 420 |
| tttcccggtt tctcctcccc ttcccgggtc attcccggta gggaggggac gaggcagggg | 480 |
| gcagagcgga tgagaaccga agatccctga ttccgtcat actcagactg ggccctcgg | 540 |
| gttttctcctg tcccctctct cacatatctc gggtttggca cccccttt ttcgccctcg | 600 |
| ccactgagga caccgactg agaggcgccc tgagcgtccc tagggctctt gtgtctctcc | 660 |
| ccatcctggc cgcgctcctg gagacccaac ttccacgcgc gagttttctc tgggcgtcct | 720 |
| cctaggcgg gcaggggaag agactgtctg gggttggccg gcagtgaccg aggacagtcg | 780 |
| agttccgcga ggtggctggg cctgagacac ggtctaaagc ggggcaaagg ggtgcccgg | 840 |
| gcgctaggcg gaggctggag ggccgggcac gctggaggt tccgggcact cacgcgcctc | 900 |
| acgctttgct ctctgcagct ccccgggatg cggtagcggc cgctgtgcgg aggccgcgaa | 960 |
| gcagctgcag ccaccgccgc gcagatccac | 990 |

<210> SEQ ID NO 7
<211> LENGTH: 1024
<212> TYPE: DNA
<213> ORGANISM: Mus musculus
<220> FEATURE:
<221> NAME/KEY: promoter
<222> LOCATION: (-97)...(927)

<400> SEQUENCE: 7

| | |
|---|---|
| ttacaagaag accggccggg cagttccagg aatcgggggg cggggcgtac tggccgggta | 60 |
| aatacccgcg cgcgcggcct ccgaggcggc tctaactctg actctacact cgcccgctcc | 120 |
| tacgaccgct gtctctccgg gctcccggac gccccttcc cggcccagct ctccgtcgag | 180 |

-continued

```
gtccctcgcc caggtccttt gcctgattcg cccaggagtg cgcctcatcg gcccggggag      240
cagcgaagcc agaggggcg cacgcacggg agccccttt gtagacttca cggctgccaa       300
catctgggcg cagcgcgagc cactgctggg cgccgcctcg cctcggggac cataggaggc      360
gcagccccaa ggccggagat ttcgcttcgg gactaggtag gaaggagggg cgcggtgtgg     420
ggaagggtgg gggcatcggt ccagctcggg agcttttccc ggtttctcct cccttcccg       480 ggtcattccc gtagggagg ggacgaggca gggggcagag cggatgagaa ccgaagatcc       540
ctgattcccg tcatactcag actggggccc tcgggtttct cctgtcccct ctctcacata     600
tctcgggttt ggcaccccc tttttcgcc ctcgccactg aggacaccgg actgagaggc      660
gccctgagcg tccctagggc tcttgtgtct ctccccatcc tggccgcgct cctggagacc     720
caacttccac gcgcgagttt tctctgggcg tcctcctagg gcgggcaggg gaagagactg     780 tctgggttg gccggcagtg accgaggaca gtcgagttcc gcgaggtggc tgggcctgag     840
acacggtcta aagcggggca aaggggtgcc ccgggcgcta ggcggaggct ggagggccgg    900
gcacgctgga gggttccggg cactcacgcg cctcacgctt tgctctctgc agctccccgg    960
gatgcggtag cggccgctgt gcggaggccg cgaagcagct gcagccaccg ccgcgcagat   1020
ccac                                                                 1024

<210> SEQ ID NO 8
<211> LENGTH: 201
<212> TYPE: DNA
<213> ORGANISM: Mus musculus
<220> FEATURE:
<221> NAME/KEY: promoter
<222> LOCATION: (-97)...(104)

<400> SEQUENCE: 8
ttacaagaag accggccggg cagttccagg aatcggggg cggggcgtac tggccgggta       60 aataccgcg cgcgcggcct ccgaggcggc tctaactctg actctacact cgcccgctcc     120
tacgaccgct gtctctccgg gctcccggac gccccttcc cggcccagct ctccgtcgag     180
gtccctcgcc caggtccttt g                                              201

<210> SEQ ID NO 9
<211> LENGTH: 1014
<212> TYPE: DNA
<213> ORGANISM: Mus musculus
<220> FEATURE:
<221> NAME/KEY: promoter
<222> LOCATION: (-87)...(927)

<400> SEQUENCE: 9
accggccggg cagttccagg aatcgggggg cggggcgtac tggccgggta aataccgcg       60 cgcgcggcct ccgaggcggc tctaactctg actctacact cgcccgctcc tacgaccgct    120
gtctctccgg gctcccggac gccccttcc cggcccagct ctccgtcgag gtccctcgcc    180
caggtccttt gcctgattcg cccaggagtg cgcctcatcg gcccggggag cagcgaagcc    240 agaggggcg cacgcacggg agccccttt gtagacttca cggctgccaa catctgggcg     300
cagcgcgagc cactgctggg cgccgcctcg cctcggggac cataggaggc gcagccccaa    360
ggccggagat ttcgcttcgg gactaggtag gaaggagggg cgcggtgtgg ggaagggtgg    420
gggcatcggt ccagctcggg agcttttccc ggtttctcct cccttcccg ggtcattccc    480 ggtagggagg ggacgaggca gggggcagag cggatgagaa ccgaagatcc ctgattcccg    540
```

```
tcatactcag actggggccc tcgggtttct cctgtcccct ctctcacata tctcgggttt      600 ggcaccccc ttttttcgcc ctcgccactg aggacaccgg actgagaggc gccctgagcg       660
tccctagggc tcttgtgtct ctccccatcc tggccgcgct cctggagacc caacttccac     720
gcgcgagttt tctctgggcg tcctcctagg gcgggcaggg aagagactg tctggggttg      780 gccggcagtg accgaggaca gtcgagttcc gcgaggtggc tggcctgag acacggtcta     840 aagcggggca aagggtgcc ccgggcgcta ggcggaggct ggagggccgg gcacgctgga      900
gggttccggg cactcacgcg cctcacgctt tgctctctgc agctccccgg gatgcggtag      960
cggccgctgt gcggaggccg cgaagcagct gcagccaccg ccgcgcagat ccac           1014

<210> SEQ ID NO 10
<211> LENGTH: 191
<212> TYPE: DNA
<213> ORGANISM: Mus musculus
<220> FEATURE:
<221> NAME/KEY: promoter
<222> LOCATION: (-87)...(104)

<400> SEQUENCE: 10
accggccggg cagttccagg aatcgggggg cgggcgtac tggccgggta aatacccgcg       60
cgcgcggcct ccgaggcggc tctaactctg actctacact cgcccgctcc tacgaccgct    120
gtctctccgg gctcccggac gccccttcc cggcccagct ctccgtcgag gtccctcgcc     180
caggtccttt g                                                          191

<210> SEQ ID NO 11
<211> LENGTH: 433
<212> TYPE: DNA
<213> ORGANISM: Mus musculus
<220> FEATURE:
<221> NAME/KEY: promoter
<222> LOCATION: (-275)...(158)

<400> SEQUENCE: 11
caggaacgct cggccaaggc tggcgccgcg cccgccggtc gggcagcctc gcgccgcgct      60
ttgtctccct ctcggtgagt ctcggcgggt cctggaggcc ccagctccaa gcccgccctc    120
cgcagcccct ccctcgccct ccgcgcacag cctttcagtg cagagtagtg actaaacatt    180
acaagaagac cggccgggca gttccaggaa tcgggggggcg gggcgtactg gccgggtaaa   240
tacccgcgcg cgcggcctcc gaggcggctc taactctgac tctacactcg cccgctccta    300
cgaccgctgt ctctccgggc tccggacgc cccttcccg gcccagctct ccgtcgaggt     360
ccctcgccca ggtcctttgc ctgattcgcc caggagtgcg cctcatcggc cggggagca     420 gcgaagccag agg                                                       433

<210> SEQ ID NO 12
<211> LENGTH: 1088
<212> TYPE: DNA
<213> ORGANISM: Mus musculus
<220> FEATURE:
<221> NAME/KEY: promoter
<222> LOCATION: (-161)...(927)

<400> SEQUENCE: 12
gccctccgca gcccctccct cgccctccgc gcacagcctt tcagtgcaga gtagtgacta     60
aacattacaa gaagaccggc cgggcagttc caggaatcgg ggggcgggc gtactggccg    120 ggtaaatacc cgcgcgcgcg gcctccgagg cggctctaac tctgactcta cactcgcccg   180
```

-continued

```
ctcctacgac cgctgtctct ccgggctccc ggacgccccc ttcccggccc agctctccgt    240
cgaggtccct cgcccaggtc ctttgcctga ttcgcccagg agtgcgcctc atcggcccgg    300
ggagcagcga agccagaggg ggcgcacgca cggggagccc ctttgtagac ttcacggctg    360
ccaacatctg ggcgcagcgc gagccactgc tgggcgccgc ctcgcctcgg ggaccatagg    420
aggcgcagcc ccaaggccgg agatttcgct tcgggactag gtaggaagga ggggcgcggt    480
gtggggaagg gtgggggcat cggtccagct cgggagcttt tcccggtttc tcctcccctt    540
cccgggtcat tcccgtgtagg gaggggacga ggcagggggc agagcggatg agaaccgaag    600
atccctgatt cccgtcatac tcagactggg gccctcgggt ttctcctgtc ccctctctca    660
catatctcgg gtttggcacc cccctttttt cgccctcgcc actgaggaca ccggactgag    720
aggcgccctg agcgtcccta gggctcttgt gtctctcccc atcctggccg cgctcctgga    780
gacccaactt ccacgcgcga gttttctctg ggcgtcctcc tagggcgggc aggggaagag    840
actgtctggg gttggccggc agtgaccgag gacagtcgag ttccgcgagg tggctgggcc    900
tgagacacgg tctaaagcgg ggcaaagggg tgccccgggc gctaggcgga ggctggaggg    960
ccgggcacgc tggagggttc cgggcactca cgcgcctcac gctttgctct ctgcagctcc   1020
ccgggatgcg gtagcggccg ctgtgcggag gccgcgaagc agctgcagcc accgccgcgc   1080
agatccac                                                           1088

<210> SEQ ID NO 13
<211> LENGTH: 9
<212> TYPE: DNA
<213> ORGANISM: Mus musculus
<220> FEATURE:
<221> NAME/KEY: promoter
<222> LOCATION: (-74)...(-66)
<223> OTHER INFORMATION: STAT-BINDING SITE AT -74 TO -66
<220> FEATURE:
<221> NAME/KEY: mutation
<222> LOCATION: (0)...(0)
<223> OTHER INFORMATION: STAT-BINDING SITE AT -74 TO -66
<220> FEATURE:
<221> NAME/KEY: promoter
<222> LOCATION: (0)...(0)
<220> FEATURE:
<221> NAME/KEY: mutation
<222> LOCATION: (0)...(0)
<223> OTHER INFORMATION: STAT-BINDING SITE AT -74 TO 66

<400> SEQUENCE: 13 ttccaggaa                                                              9

<210> SEQ ID NO 14
<211> LENGTH: 9
<212> TYPE: DNA
<213> ORGANISM: Mus musculus
<220> FEATURE:
<221> NAME/KEY: mutation
<222> LOCATION: (-74)...(-66)

<400> SEQUENCE: 14 atcgacgat                                                              9

<210> SEQ ID NO 15
<211> LENGTH: 27
<212> TYPE: DNA
<213> ORGANISM: Artificial Sequence
<220> FEATURE:
<223> OTHER INFORMATION: PRIMER

<400> SEQUENCE: 15
```
cagtagaatc cgctctcctg cagcttg                                               27

<210> SEQ ID NO 16
<211> LENGTH: 27
<212> TYPE: DNA
<213> ORGANISM: Artificial Sequence
<220> FEATURE:
<223> OTHER INFORMATION: PRIMER
<220> FEATURE:
<221> NAME/KEY: promoter
<222> LOCATION: (0)...(0)
<220> FEATURE:
<221> NAME/KEY: promoter
<222> LOCATION: (0)...(0)
<220> FEATURE:
<221> NAME/KEY: promoter
<222> LOCATION: (0)...(0)
<220> FEATURE:
<221> NAME/KEY: promoter
<222> LOCATION: (0)...(0)
<220> FEATURE:
<221> NAME/KEY: promoter
<222> LOCATION: (0)...(0)
<220> FEATURE:
<221> NAME/KEY: promoter
<222> LOCATION: (0)...(0)

<400> SEQUENCE: 16
ctcgcttttg gagctgaagg tcttgag                                               27

<210> SEQ ID NO 17
<211> LENGTH: 27
<212> TYPE: DNA
<213> ORGANISM: Artificial Sequence
<220> FEATURE:
<223> OTHER INFORMATION: PRIMER

<400> SEQUENCE: 17
cttcctacct agtcccgaag cgaaatc                                               27

<210> SEQ ID NO 18
<211> LENGTH: 26
<212> TYPE: DNA
<213> ORGANISM: Artificial Sequence
<220> FEATURE:
<223> OTHER INFORMATION: PRIMER

<400> SEQUENCE: 18
cagatgttgg cagccgtgaa gtctac                                                26

<210> SEQ ID NO 19
<211> LENGTH: 28
<212> TYPE: DNA
<213> ORGANISM: Artificial Sequence
<220> FEATURE:
<223> OTHER INFORMATION: PRIMER

<400> SEQUENCE: 19
gcgggcgagt gtagagtcag agttagag                                              28

<210> SEQ ID NO 20
<211> LENGTH: 29
<212> TYPE: DNA
<213> ORGANISM: Artificial Sequence
<220> FEATURE:
<223> OTHER INFORMATION: PRIMER

<400> SEQUENCE: 20

```
cgattcctgg aactgcccgg ccggtcttc                              29
```

<210> SEQ ID NO 21
<211> LENGTH: 29
<212> TYPE: DNA
<213> ORGANISM: Artificial Sequence
<220> FEATURE:
<223> OTHER INFORMATION: PRIMER

<400> SEQUENCE: 21

```
ctcagtgggc tttctgacct gccctcttg                              29
```

<210> SEQ ID NO 22
<211> LENGTH: 28
<212> TYPE: DNA
<213> ORGANISM: Artificial Sequence
<220> FEATURE:
<223> OTHER INFORMATION: PRIMER

<400> SEQUENCE: 22

```
gactacacag agtagcttgg gctaggag                               28
```

<210> SEQ ID NO 23
<211> LENGTH: 21
<212> TYPE: DNA
<213> ORGANISM: Artificial Sequence
<220> FEATURE:
<223> OTHER INFORMATION: SENSE PRIMER

<400> SEQUENCE: 23

```
catcgcgacg cccccgcctc t                                      21
```

<210> SEQ ID NO 24
<211> LENGTH: 22
<212> TYPE: DNA
<213> ORGANISM: Artificial Sequence
<220> FEATURE:
<223> OTHER INFORMATION: PRIMER

<400> SEQUENCE: 24

```
gaaacccgag ggccccagtc tg                                     22
```

<210> SEQ ID NO 25
<211> LENGTH: 21
<212> TYPE: DNA
<213> ORGANISM: Mus musculus
<220> FEATURE:
<221> NAME/KEY: promoter
<222> LOCATION: (-77)...(-57)

<400> SEQUENCE: 25

```
cagttccagg aatcgggggg c                                      21
```

<210> SEQ ID NO 26
<211> LENGTH: 21
<212> TYPE: DNA
<213> ORGANISM: Mus musculus
<220> FEATURE:
<221> NAME/KEY: promoter
<222> LOCATION: (0)...(0)
<223> OTHER INFORMATION: MUTATIONS AT POSITIONS -74, -71, -69, & -66

<400> SEQUENCE: 26

```
cagatcgacg attcgggggg c                                      21
```

<210> SEQ ID NO 27

```
<211> LENGTH: 26
<212> TYPE: DNA
<213> ORGANISM: Artificial Sequence
<220> FEATURE:
<223> OTHER INFORMATION: OLIGONUCLEOTIDES

<400> SEQUENCE: 27
gatcgaactg accgcccgcc gcccgt                                          26

<210> SEQ ID NO 28
<211> LENGTH: 30
<212> TYPE: DNA
<213> ORGANISM: Artificial Sequence
<220> FEATURE:
<223> OTHER INFORMATION: PRIMERS

<400> SEQUENCE: 28
gacgttccta aaagcatgca tgtcacccag                                      30

<210> SEQ ID NO 29
<211> LENGTH: 30
<212> TYPE: DNA
<213> ORGANISM: Artificial Sequence
<220> FEATURE:
<223> OTHER INFORMATION: PRIMERS

<400> SEQUENCE: 29
ggatctgcgc ggcggtggct gcagctgctt                                      30

<210> SEQ ID NO 30
<211> LENGTH: 9
<212> TYPE: DNA
<213> ORGANISM: Mus musculus
<220> FEATURE:
<221> NAME/KEY: promoter
<222> LOCATION: (-97)...(-89)
<223> OTHER INFORMATION: STAT-BINDING SITE AT -97 TO -89

<400> SEQUENCE: 30 ttacaagaa                                                              9

<210> SEQ ID NO 31
<211> LENGTH: 9
<212> TYPE: DNA
<213> ORGANISM: Artificial Sequence
<220> FEATURE:
<223> OTHER INFORMATION: n=A, T, C, or G; consensus stat-binding element

<400> SEQUENCE: 31 ttnnnnnaa                                                              9

<210> SEQ ID NO 32
<211> LENGTH: 289
<212> TYPE: DNA
<213> ORGANISM: Mus musculus
<220> FEATURE:
<221> NAME/KEY: exon
<222> LOCATION: (1)...(289)
<223> OTHER INFORMATION: Exon 1 of SOCS-3 (untranslated)

<400> SEQUENCE: 32
ctgactctac actcgcccgc tcctacgacc gctgtctctc cgggctcccg gacgccccct      60
tcccggccca gctctccgtc gaggtccctc gcccaggtcc tttgcctgat tcgcccagga    120
gtgcgcctca tcggcccggg gagcagcgaa gccagagggg cgcacgcac ggggagcccc     180 tttgtagact tcacggctgc caacatctgg gcgcagcgcg agccactgct gggcgccgcc    240
```
tcgcctcggg gaccatagga ggcgcagccc caaggccgga gatttcgct        289

<210> SEQ ID NO 33
<211> LENGTH: 564
<212> TYPE: DNA
<213> ORGANISM: Mus musculus
<220> FEATURE:
<221> NAME/KEY: intron
<222> LOCATION: (290)...(853)
<223> OTHER INFORMATION: Intron 1 of SOCS-3

<400> SEQUENCE: 33
tcgggactag gtaggaagga ggggcgcggt gtggggaagg gtgggggcat cggtccagct        60
cgggagcttt tcccggtttc tcctcccctt cccgggtcat tccggtagg gaggggacga       120
ggcaggggc agagcggatg agaaccgaag atccctgatt cccgtcatac tcagactggg       180
gccctcgggt ttctcctgtc ccctctctca catatctcgg gtttggcacc cccctttttt       240
cgccctcgcc actgaggaca ccggactgag aggcgccctg agcgtcccta gggctcttgt       300
gtctctcccc atcctggccg cgctcctgga gacccaactt ccacgcgcga gttttctctg       360
ggcgtcctcc tagggcgggc aggggaagag actgtctggg gttggccggc agtgaccgag       420
gacagtcgag ttccgcgagg tggctgggcc tgagacacgt tctaaagcgg ggcaaagggg       480
tgccccgggc gctaggcgga ggctggaggg ccgggcacgc tggagggttc cgggcactca       540
cgcgcctcac gctttgctct ctgc        564

<210> SEQ ID NO 34
<211> LENGTH: 180
<212> TYPE: DNA
<213> ORGANISM: Mus musculus
<220> FEATURE:
<221> NAME/KEY: exon
<222> LOCATION: (854)...(1033)
<223> OTHER INFORMATION: Partial exon 2 of SOCS-3

<400> SEQUENCE: 34
agctccccgg gatgcggtag cggccgctgt gcggaggccg cgaagcagct gcagccaccg        60
ccgcgcagat ccacgctggc tccgtgcgcc atggtcaccc acagcaagtt tcccgccgcc       120
gggatgagcc gccccctgga caccagcctg cgcctcaaga ccttcagctc caaaagcgag       180

<210> SEQ ID NO 35
<211> LENGTH: 3665
<212> TYPE: DNA
<213> ORGANISM: Mus musculus
<220> FEATURE:
<221> NAME/KEY: mutation
<222> LOCATION: (0)...(0)
<223> OTHER INFORMATION: promoter sequence -2759 to +927 with
      nucleotides -80 to -60 deleted

<400> SEQUENCE: 35
ccctgctggc cctgcagagg gaaggctctc ctaagcatca tctatcagaa cgtcttcaaa        60
aaaaaaaaaa aaaaaaaaa agcctctcca gccaggctag ctctaacacc atttcttccc       120
cttcccctct ctcaaattca cttatctttt tttttttttt tttttttgga ttttgagac       180
agggtttctc tgtatagccc tggttgtcct ggaactcact ttgtacacca gcctggcctc       240
gaactcagag atccacctgc ctctgcctcc tgagtgctgg gattaaaggc gtgcgccacc       300
acgcccggct aaattcactt atctatttaa tgtatataag gtataggctg cccttgaact       360
cacaaagatc tgcttgcttt gcttctggaa tactaaaggt gtgtgctacc atcacaggga       420

-continued

```
ccaagattta ttttaattct gtatatgtgt gtgtgtgtgt gtgtgtatgg ggggtgcaca    480
tgagtacaga ttcccttgga ggcctggggt ggcttaggac tggggttaca acagttgtga    540
cccatcctac ataggtcctg gcaccaacac cccccccccc cccccccgtc ttccagaagt    600
gcagcaggtg ttcttaactg ctgagccagc aatccagccc ctgacttccc tctcttactt    660
aagaagctat cacagtgtct cactgggtca caatcatgac tagtccttgc tcatggccca    720
cagcctcttc cccactgtgg gttttgcccc gcagctctgc cgccccagcg ctgcacccga    780
ggcctgacag agccaggcac gaagtcaggg tttgtggaat ggatgaatga acttgactcg    840
tggcagagca ttgtaattta caaagcactt tcccatccat taactccagg gctatttcct    900
aagagtcctc cctgtcctcc actgccctcg gctcagaggc atacggtcaa ggcagtggct    960
ggggaacact ccctgaatga gatcaaggag ggcttgttca cagagaaagg gagaatccat   1020
ttggggagcc tgagagtgac tcgaaggcaa ggactgggcc tcacctgtgg gatctccatc   1080
tgtgagcatc cgctcatcag accagtgtga gatattttaa ataaggcccc taagcctctt   1140
gactactgga attgccaggg gcgggggaca gatgggcacc catccctatt taacagataa   1200
caagactgag tccagagagg cagtgcacct gccctggtct ctcttagttc ctcagcatca   1260
gtggagcaga ttggacacag tgggccagaa gggaagcagg cagccctccc tcctagccca   1320
agctactctg tgtagtcagt ttgccctcct actggtgtta caagaagcct gtggtatcca   1380
agagggcagg tcagaaagcc cactgagagc agacactgtg tgtcacttag ctggttctca   1440
ggtggctgcc acttcctgct gcctgttgca aaactcgaca ctaggccttt atagatactc   1500
acgtgaccag gagtaaacaa cctttcacct caatcacctg ctcttatcaa tactccctct   1560 ccacccacc atcgggaaag ttcagacacc ttaaaacgta gaggcaagag agggtccatt   1620
ctgacacctc agcgactttc aggcagtggc tgaacccgtt acaacgctct gtggacagtc   1680
ctcctagtcg acattccttc tcaggtttga ccctgtcctg ggaagtgagg cttctctctc   1740
tgggttcccc actcctgttc ttgaataagg agccccacaa cctcttattc tctctataca   1800
gagcctggga aacagcaaaa ctcggctcgc ctacaagact ccagcgcgcc ctctggtgga   1860 ctcggggggac gagcatggga tgagggtttc tttcctctag ctcccccacc gcgccgagag   1920
tacctgggcg gacccacagt tcgccacgca ggttgggagg cccagatgag tgataaggta   1980
gtagttagct gctcctccca ccccactccc caaaggacat cagcacccac gtctgtcacc   2040
gaagaaccag gcaatgggcg gatgagctga ggccaggtag ctgcttctaa gtcagtgtct   2100
cctccacttc tggatctcac agcttcatct tttggacctg tctacaggta aatgtcgcgc   2160
atccccctcc tccacttcct aggtccccag tgggctggtg gctgaatggt cctacgtccc   2220
ttttggttgg cacgggatgc ttggaactgt acatgaggac ctcggggtgg cctgggtgca   2280
gagggagggg agcgtcccccg cggggatcaa agaaaggga aggggtgcca ggagggagcc   2340
tctcccggct ggcctcctag aactgcccgc gcgctcccat cgcgacgccc ccgcctctgc   2400
cagaaaccag ccttcttaga agggaggggg gggaaagtgt gaatgagaag ttggggggcgg   2460 agcgcgcggg ggaggggccg ctgccaggaa cgctcggcca aggctggcgc gcgcccgcc   2520 ggtcgggcag cctcgcgccg cgctttgtct ccctctcggt gagtctcggc gggtcctgga   2580
ggccccagct ccaagcccgc cctccgcagc ccctccctcg ccctccgcgc acagcctttc   2640
agtgcagagt agtgactaaa cattacaaga agaccggccg gcggggcgta ctggccgggt   2700
aaatacccgc gcgcgcggcc tccgaggcgg ctctaactct gactctacac tcgcccgctc   2760
```

-continued

```
ctacgaccgc tgtctctccg ggctcccgga cgcccccttc ccggcccagc tctccgtcga      2820
ggtccctcgc ccaggtcctt tgcctgattc gcccaggagt gcgcctcatc ggcccgggga      2880
gcagcgaagc cagaggggc gcacgcacgg ggagcccctt tgtagacttc acggctgcca      2940
acatctgggc gcagcgcgag ccactgctgg gcgccgcctc gcctcgggga ccataggagg      3000
cgcagcccca aggccggaga tttcgcttcg ggactaggta ggaaggaggg gcgcggtgtg      3060
gggaagggtg ggggcatcgg tccagctcgg gagcttttcc cggtttctcc tccccttccc      3120
gggtcattcc cggtagggag gggacgaggc aggggcaga gcggatgaga accgaagatc      3180
cctgattccc gtcatactca gactggggcc ctcgggtttc tcctgtcccc tctctcacat      3240
atctcgggtt tggcaccccc cttttttcgc cctcgccact gaggacaccg gactgagagg      3300
cgccctgagc gtccctaggg ctcttgtgtc tctccccatc ctggccgcgc tcctggagac      3360
ccaacttcca cgcgcgagtt ttctctgggc gtcctcctag ggcgggcagg ggaagagact      3420
gtctggggtt ggccggcagt gaccgaggac agtcgagttc cgcgaggtgg ctgggcctga      3480
gacacggtct aaagcggggc aaaggggtgc cccgggcgct aggcggaggc tggagggccg      3540
ggcacgctgg agggttccgg gcactcacgc gcctcacgct ttgctctctg cagctccccg      3600
ggatgcggta gcggccgctg tgcggaggcc gcgaagcagc tgcagccacc gccgcgcaga      3660
tccac                                                                  3665
```

<210> SEQ ID NO 36
<211> LENGTH: 3646
<212> TYPE: DNA
<213> ORGANISM: Mus musculus
<220> FEATURE:
<221> NAME/KEY: mutation
<222> LOCATION: (0)...(0)
<223> OTHER INFORMATION: promoter sequence -2759 to +927 with
      nucleotides -101 to -62 deleted

<400> SEQUENCE: 36

```
ccctgctggc cctgcagagg gaaggctctc ctaagcatca tctatcagaa cgtcttcaaa        60
aaaaaaaaaa aaaaaaaaaa agcctctcca gccaggctag ctctaacacc atttcttccc       120
cttcccctct ctcaaattca cttatctttt tttttttttt ttttttttgga ttttgagac       180 agggtttctc tgtatagccc tggttgtcct ggaactcact ttgtacacca gcctggcctc       240
gaactcagag atccacctgc ctctgcctcc tgagtgctgg gattaaaggc gtgcgccacc       300
acgcccggct aaattcactt atctatttaa tgtatatagg gtataggctg cccttgaact       360
cacaaagatc tgcttgcttt gcttctggaa tactaaaggt gtgtgctacc atcacaggga       420
ccaagattta ttttaattct gtatatgtgt gtgtgtgtgt gtgtgtatgg ggggtgcaca       480
tgagtacaga ttcccttgga ggcctgggt ggcttaggac tggggttaca acagttgtga       540
cccatcctac ataggtcctg gcaccaacac ccccccccc ccccccgtc ttccagaagt        600 gcagcaggtg ttcttaactg ctgagccagc aatccagccc ctgacttccc tctcttactt       660
aagaagctat cacagtgtct cactgggtca caatcatgac tagtccttgc tcatggccca       720
cagcctcttc cccactgtgg gttttgcccc gcagctctgc cgcccagcg ctgcacccga        780 ggcctgacag agccaggcac gaagtcaggg tttgtggaat ggatgaatga acttgactcg       840
tggcagagca ttgtaattta caaagcactt tcccatccat taactccagg gctatttcct       900
aagagtcctc cctgtcctcc actgccctcg gtcagaggc atacggtcaa ggcagtggct       960
ggggaacact ccctgaatga gatcaaggag ggcttgttca cagagaaagg gagaatccat      1020
```

-continued

```
ttggggagcc tgagagtgac tcgaaggcaa ggactgggcc tcacctgtgg gatctccatc    1080
tgtgagcatc cgctcatcag accagtgtga gatattttaa ataaggcccc taagcctctt    1140
gactactgga attgccaggg gcgggggaca gatgggcacc catccctatt taacagataa    1200
caagactgag tccagagagg cagtgcacct gccctggtct ctcttagttc ctcagcatca    1260
gtggagcaga ttggacacag tgggccagaa gggaagcagg cagccctccc tcctagccca    1320
agctactctg tgtagtcagt ttgccctcct actggtgtta caagaagcct gtggtatcca    1380
agagggcagg tcagaaagcc cactgagagc agacactgtg tgtcacttag ctggttctca    1440
ggtggctgcc acttcctgct gcctgttgca aaactcgaca ctaggccttt atagatactc    1500
acgtgaccag gagtaaacaa cctttcacct caatcacctg ctcttatcaa tactccctct    1560 ccacccccacc atcgggaaag ttcagacacc ttaaaacgta gaggcaagag agggtccatt    1620
ctgacacctc agcgactttc aggcagtggc tgaacccgtt acaacgctct gtggacagtc    1680
ctcctagtcg acattccttc tcaggtttga ccctgtcctg ggaagtgagg cttctctctc    1740
tgggttcccc actcctgttc ttgaataagg agccccacaa cctcttattc tctctataca    1800
gagcctggga aacagcaaaa ctcggctcgc ctacaagact ccagcgcgcc ctctggtgga    1860
ctcgggggac gagcatggga tgagggtttc tttcctctag ctcccccacc gcgccgagag    1920
tacctgggcg gacccacagt tcgccacgca ggttgggagg cccagatgag tgataaggta    1980
gtagttagct gctcctccca ccccactccc caaaggacat cagcacccac gtctgtcacc    2040
gaagaaccag gcaatgggcg gatgagctga ggccaggtag ctgcttctaa gtcagtgtct    2100
cctccacttc tggatctcac agcttcatct tttggacctg tctacaggta aatgtcgcgc    2160 atcccccctcc tccacttcct aggtccccag tgggctggtg gctgaatggt cctacgtccc    2220
ttttggttgg cacgggatgc ttggaactgt acatgaggac ctcggggtgg cctgggtgca    2280
gagggagggg agcgtcccccg cggggatcaa agaaaggga aggggtgcca ggagggagcc    2340
tctcccggct ggcctcctag aactgcccgc gcgctcccat cgcgacgccc ccgcctctgc    2400
cagaaaccag ccttcttaga agggagggggg gggaaagtgt gaatgagaag ttggggggcgg    2460 agcgcgcggg ggaggggccg ctgccaggaa cgctcggcca aggctggcgc gcgcccgcc    2520 ggtcgggcag cctcgcgccg cgctttgtct ccctctcggt gagtctcggc gggtcctgga    2580
ggccccagct ccaagcccgc cctccgcagc ccctccctcg ccctccgcgc acagccttc    2640 agtgcagagt agtgactagg ggcggggcgt actggccggg taaatacccg cgcgcgcggc    2700
ctccgaggcg gctctaactc tgactctaca ctcgcccgct cctacgaccg ctgtctctcc    2760
gggctcccgg acgccccctt ccggcccag ctctccgtcg aggtccctcg cccaggtcct    2820
ttgcctgatt cgcccaggag tgcgcctcat cggcccgggg agcagcgaag ccagaggggg    2880
cgcacgcacg gggagcccct ttgtagactt cacggctgcc aacatctggg cgcagcgcga    2940
gccactgctg ggcgccgcct cgcctcgggg accataggag gcgcagcccc aaggccggag    3000
atttcgcttc gggactaggt aggaaggagg ggcgcggtgt gggggaagggt gggggcatcg    3060 gtccagctcg ggagcttttc ccggtttctc ctcccccttcc cgggtcattc ccgtagggga    3120
ggggacgagg caggggggcag agcggatgag aaccgaagat ccctgattcc cgtcatactc    3180 agactgggggc cctcgggttt ctcctgtccc ctctctcaca tatctcgggt ttggcacccc    3240
ccttttttcg ccctcgccac tgaggacacc ggactgagag gcgccctgag cgtccctagg    3300
gctcttgtgt ctctccccat cctggccgcg ctcctggaga cccaacttcc acgcgcgagt    3360
tttctctggg cgtcctccta gggcgggcag gggaagagac tgtctggggt tggccggcag    3420
```

-continued

```
tgaccgagga cagtcgagtt ccgcgaggtg gctgggcctg agacacggtc taaagcgggg      3480
caaaggggtg ccccgggcgc taggcggagg ctggagggcc gggcacgctg gagggttccg      3540
ggcactcacg cgcctcacgc tttgctctct gcagctcccc gggatgcggt agcggccgct      3600
gtgcggaggc cgcgaagcag ctgcagccac cgccgcgcag atccac                    3646
```

<210> SEQ ID NO 37
<211> LENGTH: 3686
<212> TYPE: DNA
<213> ORGANISM: Mus musculus
<220> FEATURE:
<221> NAME/KEY: mutation
<222> LOCATION: (0)...(0)
<223> OTHER INFORMATION: promoter sequence -2759 to +927 with
      nucleotide at position -74 mutated from T to A, nucleotide at
      position -71 mutated from C to G, nucleotide at
      position -69 mutated from G to C, and nucleotide
      at position -66 mutated from A to T

<400> SEQUENCE: 37

```
ccctgctggc cctgcagagg gaaggctctc ctaagcatca tctatcagaa cgtcttcaaa      60
aaaaaaaaaa aaaaaaaaaa agcctctcca gccaggctag ctctaacacc atttcttccc     120
cttcccctct ctcaaattca cttatctttt tttttttttt ttttttttgga ttttgagac     180 agggtttctc tgtatagccc tggttgtcct ggaactcact ttgtacacca gcctggcctc     240
gaactcagag atccacctgc ctctgcctcc tgagtgctgg gattaaaggc gtgcgccacc     300
acgcccggct aaattcactt atctatttaa tgtatatagg gtataggctg cccttgaact     360
cacaaagatc tgcttgcttt gcttctggaa tactaaaggt gtgtgctacc atcacaggga     420
ccaagattta ttttaattct gtatatgtgt gtgtgtgtgt gtgtgtatgg gggtgcaca      480 tgagtacaga ttcccttgga ggcctggggt ggcttaggac tggggttaca acagttgtga     540
cccatcctac ataggtcctg gcaccaacac cccccccccc cccccccgtc ttccagaagt     600
gcagcaggtg ttcttaactg ctgagccagc aatccagccc ctgacttccc tctcttactt     660
aagaagctat cacagtgtct cactgggtca caatcatgac tagtccttgc tcatggccca     720
cagcctcttc cccactgtgg gttttgcccc gcagctctgc cgcccagcg ctgcacccga      780 ggcctgacag agccaggcac gaagtcaggg tttgtggaat ggatgaatga acttgactcg     840
tggcagagca ttgtaattta caaagcactt tcccatccat taactccagg gctatttcct     900
aagagtcctc cctgtcctcc actgcccccg gctcagaggc atacggtcaa ggcagtggct     960
ggggaacact ccctgaatga gatcaaggag ggcttgttca cagagaaagg gagaatccat    1020
ttggggagcc tgagagtgac tcgaaggcaa ggactgggcc tcacctgtgg gatctccatc    1080
tgtgagcatc cgctcatcag accagtgtga gatattttaa ataaggcccc taagcctctt    1140
gactactgga attgccaggg gcgggggaca gatgggcacc catccctatt taacagataa    1200
caagactgag tccagagagg cagtgcacct gccctggtct ctcttagttc ctcagcatca    1260
gtggagcaga ttggacacag tgggccagaa gggaagcagg cagccctccc tcctagccca    1320
agctactctg tgtagtcagt ttgccctcct actggtgtta caagaagcct gtggtatcca    1380
agagggcagg tcagaaagcc cactgagagc agacactgtg tgtcacttag ctggttctca    1440
ggtggctgcc acttcctgct gcctgttgca aaactcgaca ctaggccttt atagatactc    1500
acgtgaccag gagtaaacaa cctttcacct caatcacctg ctcttatcaa tactccctct    1560
ccaccccacc atcgggaaag ttcagacacc ttaaaacgta gaggcaagag agggtccatt    1620
```

```
ctgacacctc agcgactttc aggcagtggc tgaacccgtt acaacgctct gtggacagtc      1680
ctcctagtcg acattccttc tcaggtttga ccctgtcctg ggaagtgagg cttctctctc      1740
tgggttcccc actcctgttc ttgaataagg agccccacaa cctcttattc tctctataca      1800
gagcctggga aacagcaaaa ctcggctcgc ctacaagact ccagcgcgcc ctctggtgga      1860
ctcgggggac gagcatggga tgagggtttc tttcctctag ctcccccacc gcgccgagag      1920
tacctgggcg gacccacagt tcgccacgca ggttgggagg cccagatgag tgataaggta      1980
gtagttagct gctcctccca ccccactccc caaaggacat cagcacccac gtctgtcacc      2040
gaagaaccag gcaatgggcg gatgagctga ggccaggtag ctgcttctaa gtcagtgtct      2100
cctccacttc tggatctcac agcttcatct tttggacctg tctacaggta aatgtcgcgc      2160 atcccctcc  tccacttcct aggtccccag tgggctggtg gctgaatggt cctacgtccc      2220
ttttggttgg cacgggatgc ttggaactgt acatgaggac ctcggggtgg cctgggtgca      2280
gagggagggg agcgtccccg cggggatcaa agaaaggga  agggtgcca  ggagggagcc      2340 tctcccggct ggcctcctag aactgcccgc gcgctcccat cgcgacgccc ccgcctctgc      2400
cagaaaccag ccttcttaga agggaggggg gggaaagtgt gaatgagaag ttggggggcgg     2460 agcgcgcggg ggagggggccc ctgccaggaa cgctcggcca aggctggcgc cgcgcccgcc    2520
ggtcgggcag cctcgcgccg cgctttgtct ccctctcggt gagtctcggc gggtcctgga      2580
ggccccagct ccaagcccgc cctccgcagc ccctccctcg ccctccgcgc acagcctttc      2640
agtgcagagt agtgactaaa cattacaaga agaccggccc ggcagatcga cgattcgggg      2700
ggcggggcgt actggccggg taaatacccg cgcgcgcggc ctccgaggcg gctctaactc      2760
tgactctaca ctcgcccgct cctacgaccg ctgtctctcc gggctcccgg acgcccccttt     2820 cccggcccag ctctccgtcg aggtccctcg cccaggtcct ttgcctgatt cgcccaggag     2880
tgcgcctcat cggcccgggg agcagcgaag ccagaggggg cgcacgcacg gggagccccct   2940 ttgtagactt cacggctgcc aacatctggg cgcagcgcga ccactgctg ggcgccgcct       3000 cgcctcgggg accataggag gcgcagcccc aaggccggag atttcgcttc gggactaggt      3060
aggaaggagg ggcgcggtgt ggggaagggt gggggcatcg gtccagctcg ggagcttttc     3120
ccggtttctc ctcccctccc cggtcattc  ccggtaggga ggggacgagg caggggcag      3180 agcggatgag aaccgaagat ccctgattcc cgtcatactc agactggggc cctcgggttt      3240
ctcctgtccc ctctctcaca tatctcgggt ttggcacccc ccttttttcg ccctcgccac      3300
tgaggacacc ggactgagag gcgccctgag cgtccctagg gctcttgtgt ctctccccat      3360
cctggccgcg ctcctggaga cccaacttcc acgcgcgagt tttctctggg cgtcctccta      3420
gggcgggcag gggaagagac tgtctggggt tggccggcag tgaccgagga cagtcgagtt      3480
ccgcgaggtg gctgggcctg agacacggtc taaagcgggg caaaggggtg ccccgggcgc     3540
taggcggagg ctggagggcc gggcacgctg gagggttccg ggcactcacg cgcctcacgc     3600
tttgctctct gcagctcccc gggatgcggt agcggccgct gtgcggaggc cgcgaagcag    3660
ctgcagccac cgccgcgcag atccac                                           3686
```

<210> SEQ ID NO 38
<211> LENGTH: 2044
<212> TYPE: DNA
<213> ORGANISM: Mus musculus
<220> FEATURE:
<221> NAME/KEY: promoter
<222> LOCATION: (-2759)...(-716)

<400> SEQUENCE: 38

```
ccctgctggc cctgcagagg gaaggctctc ctaagcatca tctatcagaa cgtcttcaaa       60
aaaaaaaaaa aaaaaaaaaa agcctctcca gccaggctag ctctaacacc atttcttccc      120
cttcccctct ctcaaattca cttatctttt tttttttttt tttttttgga tttttgagac      180
agggtttctc tgtatagccc tggttgtcct ggaactcact tgtacacca gcctggcctc       240
gaactcagag atccacctgc ctctgcctcc tgagtgctgg gattaaaggc gtgcgccacc      300
acgcccggct aaattcactt atctatttaa tgtatatagg gtataggctg cccttgaact      360
cacaaagatc tgcttgcttt gcttctggaa tactaaaggt gtgtgctacc atcacaggga      420
ccaagattta ttttaattct gtatatgtgt gtgtgtgtgt gtgtgtatgg ggggtgcaca      480
tgagtacaga ttcccttgga ggcctggggt ggcttaggac tggggttaca acagttgtga      540
cccatcctac ataggtcctg gcaccaacac cccccccccc cccccccgtc ttccagaagt      600
gcagcaggtg ttcttaactg ctgagccagc aatccagccc ctgacttccc tctcttactt      660
aagaagctat cacagtgtct cactgggtca caatcatgac tagtccttgc tcatggccca      720
cagcctcttc cccactgtgg gttttgcccc gcagctctgc cgccccagcg ctgcacccga      780
ggcctgacag agccaggcac gaagtcaggg tttgtggaat ggatgaatga acttgactcg      840
tggcagagca ttgtaattta caaagcactt tcccatccat taactccagg gctatttcct      900
aagagtcctc cctgtcctcc actgccctcg gctcagaggc atacggtcaa ggcagtggct      960
ggggaacact ccctgaatga gatcaaggag ggcttgttca cagagaaagg gagaatccat     1020
ttggggagcc tgagagtgac tcgaaggcaa ggactgggcc tcacctgtgg gatctccatc     1080
tgtgagcatc cgctcatcag accagtgtga gatattttaa ataaggcccc taagcctctt     1140
gactactgga attgccaggg gcgggggaca gatgggcacc catccctatt aacagataa      1200
caagactgag tccagagagg cagtgcacct gccctggtct ctcttagttc ctcagcatca     1260
gtggagcaga ttggacacag tgggccagaa gggaagcagg cagccctccc tcctagccca     1320
agctactctg tgtagtcagt ttgccctcct actggtgtta caagaagcct gtggtatcca     1380
agagggcagg tcagaaagcc cactgagagc agacactgtg tgtcacttag ctggttctca     1440
ggtggctgcc acttcctgct gcctgttgca aaactcgaca ctaggccttt atagatactc     1500
acgtgaccag gagtaaacaa cctttcacct caatcacctg ctcttatcaa tactccctct     1560
ccaccccacc atcgggaaag ttcagacacc ttaaaacgta gaggcaagag agggtccatt     1620
ctgacacctc agcgactttc aggcagtggc tgaacccgtt acaacgctct gtggacagtc     1680
ctccagtcg acattccttc tcaggtttga ccctgtcctg ggaagtgagg cttctctctc      1740
tgggttcccc actcctgttc ttgaataagg agccccacaa cctcttattc tctctataca     1800
gagcctggga aacagcaaaa ctcggctcgc ctacaagact ccagcgcgcc ctctggtgga     1860
ctcgggggac gagcatggga tgagggtttc tttcctctag ctcccccacc gcgccgagag     1920
tacctgggcg gacccacagt tcgccacgca ggttgggagg cccagatgag tgataaggta     1980
gtagttagct gctcctccca ccccactccc caaaggacat cagcacccac gtctgtcacc     2040
gaag                                                                  2044
```

<210> SEQ ID NO 39
<211> LENGTH: 433
<212> TYPE: DNA
<213> ORGANISM: Mus musculus
<220> FEATURE:
<221> NAME/KEY: promoter -continued

<222> LOCATION: (-275)...(158)

<400> SEQUENCE: 39

```
caggaacgct cggccaaggc tggcgccgcg cccgccggtc gggcagcctc gcgccgcgct      60
ttgtctccct ctcggtgagt ctcggcgggt cctggaggcc ccagctccaa gcccgccctc     120
cgcagcccct ccctcgccct ccgcgcacag cctttcagtg cagagtagtg actaaacatt    180
acaagaagac cggccgggca gttccaggaa tcgggggcg gggcgtactg gccgggtaaa     240
tacccgcgcg cgcggcctcc gaggcggctc taactctgac tctacactcg cccgctccta    300
cgaccgctgt ctctccgggc tcccggacgc ccccttcccg gcccagctct ccgtcgaggt    360
ccctcgccca ggtcctttgc ctgattcgcc caggagtgcg cctcatcggc ccggggagca    420
gcgaagccag agg                                                        433
```

SUPPRESSOR OF CYTOKINE SIGNALING (SOCS)-3 PROMOTER AND METHODS FOR ITS USE IN GENETIC THERAPY IN HUMANS

The U.S. Government has a paid-up license in this invention and the right in limited circumstances to require the patent owner to license others on reasonable terms as provided for by the terms of grant DK 50238 awarded by the NIH.

BACKGROUND OF THE INVENTION

Throughout this application various publications are referenced within parentheses. The disclosures of these publications in their entireties are hereby incorporated by reference in this application in order to more fully describe the state of the art to which this invention pertains. 1. The Field of the Invention This invention relates to the medical arts. In particular the present invention relates to the field of cellular signal transduction and to gene therapy.

2. Discussion of the Rekated Art

Cytokines are small secreted proteins or factors (5 to 20 kD) that have specific effects on cell-to-cell interactions, intercellular communication, or the behavior of other cells. Cytokines involved in inflammatory diseases are produced by lymphocytes, especially $T_H1$ and $T_H2$ lymphocytes, monocytes, intestinal macrophages, granulocytes, epithelial cells, and fibroblasts. (Reviewed in G. Rogler and T. Andus, *Cytokines in inflammatory bowel disease*, World J. Surg. 22(4):382–89 [1998]; H. F. Galley and N. R. Webster, *The immuno-inflammatory cascade*, Br. J. Anaesth. 77:11–16 [1996]). Some cytokines are pro-inflammatory (e.g., tumor necrosis factor [TNF]-α, interleukin [IL]-1 (αand β), IL-6, IL-8, IL-12); others are anti-inflammatory (e.g., IL-1 receptor antagonist [IL-1ra], IL-4, IL-10, IL-11, and transforming growth factor [TGF]-β). However, there may be overlap and functional redundancy in their effects under certain inflammatory conditions.

One group of cytokines, the IL-6-type, are also important in the regulation of complex cellular processes such as gene activation, proliferation and differentiation. The IL-6-type cytokines include IL-6, IL-11, leukemia inhibitory factor (LIF), oncostatin M, ciliary neutrophic factor, and cardiotrophin-1. (Reviewed in P. C. Heinrich et al., *Interleukin-6-type cytokine signaling through the gp130/JAK/STAT pathway*, Biochem. J. 334(Pt 2):297–314 [1998]). The IL-6-type cytokines (also known as the gp130 signaling subunit cytokine family) have in common that signal transduction proceeds through a pathway beginning with ligand binding by type I and type II surface receptors, internalization involving affinity converter/signal transducing subunit gp130, the activation of the Janus family of cytoplasmic tyrosine kinases (e.g., Jak1, Jak2, and Tyk2); this results in the phosphorylation and dimerization of the signal transducers and activators of transcription (STAT)-1 and STAT-3 that activate transcription from promoters having STAT recognition sites. (Heinrich et al. [1998]; M. Ernst et al., *Gp130-mediated signal transduction in embryonic stem cells involves activation of Jak and Ras/mitogen-activated protein kinase pathways*, J. Biol. Chem. 271(47):30136–43 [1996]; R. Starr et al., *A family of cytokine-inducible inhibitors of signaling*, Nature 387(6636):917–21 [1997]; T. Hirano et al., Cytokine & Growth Factor Rev. 8:241–52 [1997]; E. Arzt & G. K. Stalla, Neuroimmunomodulation 3:28–34 [1996]; S. J. Haque & B. R. G. Williams, Semin. Oncol. 25 (suppl. 1):14–22 [1998]). This pathway is known as the Jak-STAT signaling cascade.

Several IL-6-type cytokines are important neuro-immuno-endocrine modulators of the hypothalamo-pituitary-adrenal (HPA) axis (Arzt, E. & Stalla [1996]; S. Melmed, Trends Endocrinol. Metab. 8:391–97 [1997]; H. O. Besedovsky, & A. Del Rey, Endo. Rev. 17:64–102 [1996]), which regulates metabolism, including growth, body temperature, water balance, blood sugar, fat metabolism, and sexual and nerve function. For example, LIF is a potent auto-paracrine stimulus of pituitary proopiomelanocortin (POMC) gene expression and adrenocorticotrophic hormone (ACTH) secretion, which stimulates the adrenals to produce additional hormones. Thus, LIF modulates the HPA axis response to various inflammatory and stress stimuli. (Z. Wang et al., Endocrinology 137:2947–53 [1996]; C. J. Auernhammer et al., Endocrinology 139:2201–08 [1998a]). In vitro experiments using human fetal pituitary cells (I. Shimon et al., *J. Clin. Invest.* 100: 357–63 [1997]) and the corticotroph cell line AtT-20 (S. Akita et al., *J. Clin., Invest* 95, 1288–1298 [1995]; C. Bousquet et al., J. Biol. Chem 272:10551–57 [1997]), showed a profound and synergistic action of LIF and corticotropin-releasing hormone (CRH) on POMC gene expression and ACTH secretion. LIF is known to induce the Jak-STAT signaling cascade in the corticotroph cells. (C. J. Auernhammer et al., *Pituitary corticotroph SOCS-3: novel intracellular regulation of leukemia-inhibitory factor-mediated proopiomelanocortin gene expression and adrenocorticotropin secretion*, Mol. Endocrinol. 12(7):954–61 [1998b]; I. Shimon et al. [1997]; D. W. Ray et al., *Leukemia inhibitory factor (LIF) stimulates proopiomelanocortin (POMC) expression in a corticotroph cell line. Role of STAT pathway*, J. Clin. Invest. 97(8):1852–59 [1996]; D. W. Ray et al., Ann. N.Y. Acad. Sci. USA 840:162–73 [1998]).

A new family of cytokine-inducible proteins has recently been described that inhibits the Jak-STAT signaling cascade. (E.g., S. E. Nicholson et al., *The SOCS proteins: a new family of negative regulators of signal transduction*, J. Leukoc. Biol. 63(6):665–68 [1998]; R. Starr et al., *SOCS: suppressors of cytokine signaling*, Int. J. Biochem. Cell. Biol. 30(10):1081–85 [1998]). These proteins have been variously termed suppressors of cytokine signaling ("SOCS")(R. Starr et al., *A family of cytokine-inducible inhibitors of signaling*, Nature 387(6636):917–21 [1998]; D. J. Hilton et al., Proc. Natl. Acad. Sci. USA 95:114–19 [1998]), STAT-induced STAT inhibitors (SSI)(T. Naka et al., Nature 387:924–28 [1997]; S. Minamoto et al., Biochem. Biophys. Res. Commun 237:79–83 [1997]), cytokine-inducible SH2 containing protein (CIS)(A. Yoshimura et al., EMBO J. 14:2816–26 [1995]; M. Masuhara et al., Biochem. Biophys. Res,. Commun. 239:439–46 [1997]; A, Matsumoto et al., Blood 89:3148–54 [1997]), and Jak binding protein (JAB)(T. A. Endo et al., Nature 387:921–24 [1997]; H. Sakamoto et al., Blood 92:1668–76 [1998]). The SOCS-protein family currently consists of CIS and SOCS-1 through 7. (D. J. Hilton et al. [1998]; M. J. Aman & W. J. Leonard, Curr. Biol. 7:R784–R788 [1997]; R. Starr & D. J. Hilton, Int. J. Biochem. Cell Biol. 30:1081–85 [1998]).

SOCS-protein expression is stimulated by various cytokines in a tissue specific manner (R. Starr et al., Nature 387:917–21 [1997]; M. J. Aman & W. J. Leonard [1997]; H. Sakamoto et al. [1998]; H. O. Besedovsky, & A. Del Rey [1996]; T. E. Adams et al., J. Biol. Chem. 273:1285–87 [1998]; C. Bjorbaek et al., Mol. Cell 1:619–625 [1998]). The gene expression of SOCS-1/SSI-1/JAB and SOCS-3/SSI-3/CIS-3, referred to herein as SOCS-1 and SOCS-3, are induced by IL-6 and LIF in various tissues (R. Starr et al. [1997]; D. J. Hilton et al. [1998]; T. Naka et al. [1997]; S. Minamoto et al. [1997]; M. Masuhara et al. [1997]; A. Matsumoto et al. [1997]; T. A. Endo et al. [1997]). For example, SOCS-3 gene expression is rapidly induced by LIF in the pituitary in vivo, and in corticotroph AtT-20 cells in vitro. (C. J. Auernhammer et al. [1998b]).

Both, SOCS-1 and SOCS-3 proteins bind to the JH1 domain of Jak-2 and thereby inhibit IL-6-, IL-11-, or LIF-induced tyrosine phosphorylation activity by Jak-2 of gp130 and STAT-3. (S. Minamoto et al. [1997]; M. Masuhara et al. [1997]; C. J. Auernhammer et al. [1998b]). SOCS-3 is induced by growth hormone (GH) in the liver, and inhibits GH-induced Spi 2.1 promoter activity. (T. E. Adams et al. [1998]). SOCS-3 inhibits LIF-induced POMC gene expression and ACTH secretion (C. J. Auernhammer et al. [1998b]), thus providing an intracellular negative feedback regulation of cytokine-induced activation of the HPA-axis. Hypothalamic SOCS-3 gene expression is stimulated by leptin, and SOCS-3 inhibits leptin-induced signal transduction (C. Bjorbaek et al., Mol. Cell 1:619–625 [1998]), thus suggesting its regulatory role in central leptin resistance.

The structure of SOCS proteins has been described. (e.g., S. E. Nicholson et al., *Mutational analyses of the SOCS proteins suggest a dual domain requirement but distinct mechanisms for inhibition of LIF and IL-6 signal transduction*, EMBO J. 18(2):375–85 (January 1999). Dominant negative STAT-3 mutants, isolated by substitution of a carboxy-terminal tyrosine phosphorylation site $Tyr^{705}$ to $Phe^{705}$ (STAT-3F) or mutation at positions important for DNA binding (STAT-3D) have been recently described (K. Nakajima et al., EMBO J. 15:3651–58 [1996]). Overexpression of these STAT-3 dominant negative mutants in corticotroph AtT-20 cells inhibits LIF-induced POMC gene expression and ACTH secretion. (C. Bousquet & S. Melmed, J. Biol. Chem. 274:10723–30 [1999]). Cytokine-induced gene expression of SOCS-1 has been shown to be inhibited in cells overexpressing dominant negative STAT-3 mutants (T. Naka et al. [1997]), but the promoter region of SOCS-1 has not been cloned.

Therefore, there remains a definite need for a promoter sequence capable of regulating expression of preselected proteins, such as SOCS-3 protein, and that can be targeted by gene therapy to treat growth disorders, autoimmune diseases, immune diseases, and inflammatory conditions. This and other features and benefits provided by the present invention will now be described.

SUMMARY OF THE INVENTION

The present invention relates to a nucleic acid construct comprising a murine SOCS-3 promoter sequence, or a non-murine homologue thereof, or an operative fragment or derivative of any of these. The construct can also contain, operatively linked to the SOCS-3 promoter, a DNA sequence encoding a gene for any preselected protein or a gene-specific part of such a DNA sequence, or to a DNA sequence that encodes a preselected gene-specific antisense RNA or a catalytic RNA. A preselected protein that is encoded by the nucleic acid construct can be from an autologous, allogeneic, or xenogeneic source. In addition, the present nucleic acid construct optionally contains a reporter gene to facilitate detection and/or selection of successfully transfected cells. The present nucleic acid construct is particularly useful for linking expression of a desired gene product to physiological processes that are regulated by gp130-mediated signal transduction from IL-6-type cytokines (i.e., cytokines of the gp130 signaling subunit cytokine family), such as IL-6, IL-11, or LIF. For example, when the encoded protein is a SOCS-3 protein, the present nucleic acid can be used to modulate the physiology and/or hormonal secretions of cells of the hypothalamus, pituitary, adrenals, liver, or other tissues, through a negative autoregulatory feedback of SOCS-3 on its own cytokine-induced gene expression.

The present invention also relates to a transgenic vertebrate cell containing the nucleic acid construct of the present invention and to transgenic non-human vertebrates comprising such cells.

The present invention also relates to a method of treating a growth retardation disorder in a human subject. The method involves genetically modifying a GH-responsive or gp130-responsive cell(s) of a human subject having a growth retardation disorder, such as dwarfism, GH deficiency, gonadal dysgenesis, chondrodystrophy, or bone-cartilage dysplasia. The cell(s) are genetically modified using a nucleic acid construct that comprises a SOCS-3 promoter sequence, or operative fragment thereof, operatively linked to a DNA sequence that encodes an RNA that specifically hybridizes to a functional SOCS-3 mRNA. In response to a growth-inducing cytokine, in vivo, the genetically modified cell(s) within the human subject, transcribe an RNA transcript that specifically hybridizes to a functional SOCS-3 mRNA, preventing translation therefrom. This RNA transcript can be an antisense RNA or a catalytic RNA (ribozyme) that cleave the SOCS-3 mRNA. As a consequence, the amount of SOCS-3 protein produced within the genetically modified cell(s) is relatively reduced, and one or more symptoms of the growth retardation disorder in the subject are thereby improved, due to a lessening of SOCS-3-mediated signal suppression within the genetically modified cell(s).

The present invention also relates to a method of treating a growth acceleration disorder in a human subject. The method involves genetically modifying a GH-responsive or gp130-responsive cell(s) of a human subject having a growth acceleration disorder, such as gigantism, acromegaly, or Cushing's disease. The cell(s) are genetically modified using a nucleic acid construct, comprising a SOCS-3 promoter sequence, or operative fragment thereof, operatively linked to a DNA sequence encoding a SOCS-3 protein, or functional fragment thereof. In response to the growth-inducing cytokine, in vivo, the genetically modified cell(s) produce an enhanced amount of SOCS-3 protein. The symptom(s) of the growth acceleration disorder in the subject are thereby improved, due to enhanced SOCS-3-mediated cytokine signal suppression.

The present invention also relates to a method of treating an autoimmune disease, immune disease, or inflammatory condition in a human subject having a condition, such as Crohn's disease, ulcerative colitis, multiple sclerosis, systemic lupus erythematosus, rheumatoid arthritis, Grave's disease, or a neuroendocrinological response to psychological or physical stress. The method involves genetically modifying a gp130-responsive cell(s), responsive to a pro-inflammatory cytokine, such as IL-6 or LIF. The cell(s) are genetically modified using a nucleic acid construct that includes a SOCS-3 promoter sequence, or operative fragment thereof, operatively linked to a DNA sequence encoding a SOCS-3 protein, or functional fragment thereof. In response to a pro-inflammatory cytokine of the gp130 signaling subunit cytokine family, in vivo, the genetically modified cell(s) produce an enhanced amount of SOCS-3 protein. The symptom(s) of the autoimmune disease, immune disease, or inflammatory condition in the subject are thereby improved, due to a relative increase in SOCS-3-mediated signal suppression.

Alternatively, the SOCS-3 promoter is operatively linked to a DNA sequence encoding a functional anti-inflammatory cytokine of the gp130 signaling subunit cytokine family, such as IL-11, linked to a functional secretory signal. In response to a pro-inflammatory cytokine of the gp130 signaling subunit cytokine family, in vivo, the genetically modified cell(s) produce and secrete an enhanced amount of the anti-inflammatory cytokine. The symptom(s) of the autoimmune disease, immune disease, or inflammatory condition in the subject are thereby improved.

The present invention also relates to a kit for genetically modifying a vertebrate cell. The kit includes a polynucleotide comprising a murine SOCS-3 promoter sequence having SEQ. ID. NO.:1, or an operative fragment or non-murine homologue thereof, or an operative derivative of any of these. Preferably, the polynucleotide includes, operatively linked to the SOCS-3 promoter, at least one DNA sequence encoding a preselected protein or a gene-specific part of such a DNA sequence, or a DNA encoding a preselected gene-specific antisense RNA or a specific catalytic RNA, as appropriate for a particular application. Optionally, the promoter is linked to a reporter gene for facilitating detection, isolation, or selection of genetically modified cells from unmodified cells. Some embodiments of the kit are configured for use in practicing the present methods of treating a growth retardation or acceleration disorder in a human subject or the present method of treating an autoimmune disease, immune disease, or inflammatory condition in a human subject.

These and other advantages and features of the present invention will be described more fully in a detailed description of the preferred embodiments which follows.

BRIEF DESCRIPTION OF THE DRAWINGS

FIG. 1 shows stimulation of expression from the murine SOCS-3 promoter in corticotroph AtT-20 cells treated with $0.5 \times 10^{-9}$ M LIF, IL-6, or IL-11 for 60 and 120 min, respectively.

FIG. 2 shows LIF-induced SOCS-3 promoter activity and gene expression in corticotroph AtT-20 cells overexpressing wild type STAT-3 (AtT-20W) or dominant negative STAT-3 mutants (AtT-20F and AtT-20D), as well as wild type SOCS-3 (AtT-20S) and mock-transfected (AtT-20M); cells were treated with $0.5 \times 10^{-9}$ M LIF for 45 min.

DETAILED DESCRIPTION OF THE SPECIFIC EMBODIMENTS

Figure 1A:
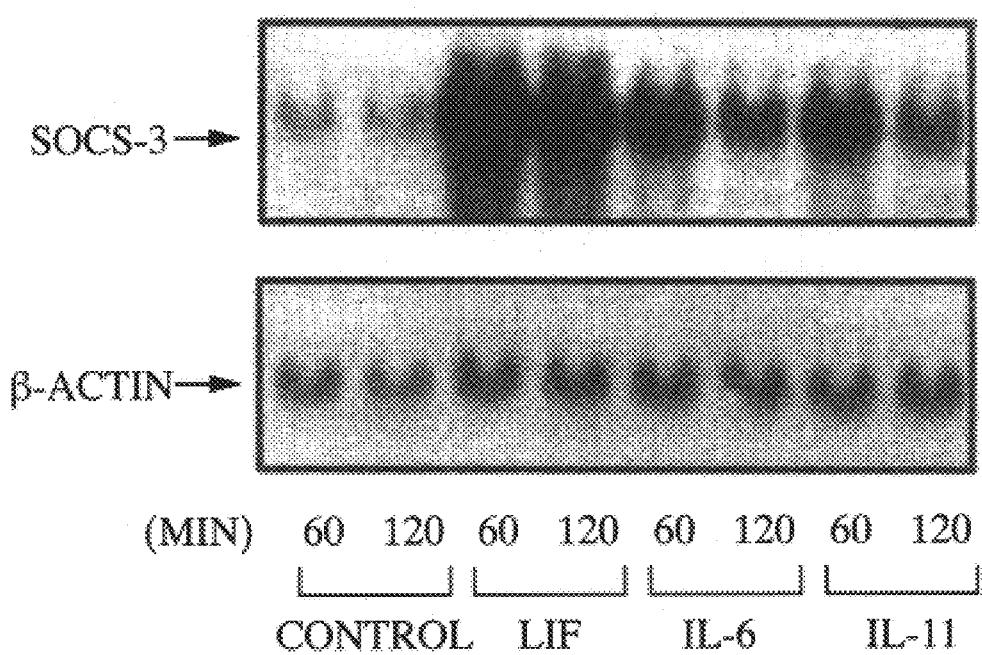
FIG. 1A shows a Northern blot analysis performed with 25 μg total RNA per lane. The upper panel shows SOCS-3 mRNA; the lower panel shows β-actin mRNA.

The present invention relates to a nucleic acid construct comprising a murine SOCS-3 promoter sequence, or an operative fragment thereof, or a non-murine homologue thereof, or an operative derivative of any of these.

The following nucleotide sequence represents the full length ~3.8-kb genomic 5'-region of the murine SOCS-3 gene (GenBank Accession AF117732). The transcription start site is defined as +1. An untranscribed region extends from nucleotide −2907 to −1, inclusive. A transcribed but untranslated region (exon 1) extends from +1 to +289; exon 2, begins at +854 ( exons are underlined), and contains the intronless coding region of SOCS-3 with a translational start site encoded at nt. +944 to +946. (R. Starr et al. [1997]). The translation initiation codon ATG (nt. +944 to +946) and a TATA-box (nt. −39 to −34) are indicated in boldface type. Two potential STAT-binding elements (nt. −74 to −66 and nt. −97 to −88) are in boldface underlined:

```
-2907 GACGTTCCTA AAAGCATGCA TGTCACCCAG CTTACCCACC CATCTCAGGC CACAGCAGCC

-2847 TGAGAGAGCG GAAGAACACC TGCTGGTCCT GTCCCACCTC TCCTCTTCAA ACAGCCCCAC

-2787 ATCCTCCAGT TTTGCTCTGG GTGGAGCTCC CTGCTGGCCC TGCAGAGGGA AGGCTCTCCT

-2727 AAGCATCATC TATCAGAACG TCTTCAAAAA AAAAAAAAAA AAAAAAAAAG CCTCTCCAGC

-2667 CAGGCTAGCT CTAACACCAT TTCTTCCCCT TCCCCTCTCT CAAATTCACT TATCTTTTTT

-2607 TTTTTTTTTT TTTTTGGATT TTTGAGACAG GGTTTCTCTG TATAGCCCTG GTTGTCCTGG

-2547 AACTCACTTT GTACACCAGC CTGGCCTCGA ACTCAGAGAT CCACCTGCCT CTGCCTCCTG

-2487 AGTGCTGGGA TTAAAGGCGT GCGCCACCAC GCCCGGCTAA ATTCACTTAT CTATTTAATG
```

-continued

```
-2427 TATATAGGGT ATAGGCTGCC CTTGAACTCA CAAAGATCTG CTTGCTTTGC TTCTGGAATA
-2367 CTAAAGGTGT GTGCTACCAT CACAGGGACC AAGATTTATT TTAATTCTGT ATATGTGTGT
-2307 GTGTGTGTGT GTGTATGGGG GGTGCACATG AGTACAGATT CCCTTGGAGG CCTGGGGTGG
-2247 CTTAGGACTG GGGTTACAAC AGTTGTGACC CATCCTACAT AGGTCCTGGC ACCAACACCC
-2187 CCCCCCCCCC CCCCCGTCTT CCAGAAGTGC AGCAGGTGTT CTTAACTGCT GAGCCAGCAA
-2127 TCCAGCCCCT GACTTCCCTC TCTTACTTAA GAAGCTATCA CAGTGTCTCA CTGGGTCACA
-2067 ATCATGACTA GTCCTTGCTC ATGGCCCACA GCCTCTTCCC CACTGTGGGT TTTGCCCCGC
-2007 AGCTCTGCCG CCCCAGCGCT GCACCCGAGG CCTGACAGAG CCAGGCACGA AGTCAGGGTT
-1947 TGTGGAATGG ATGAATGAAC TTGACTCGTG GCAGAGCATT GTAATTTACA AAGCACTTTC
-1887 CCATCCATTA ACTCCAGGGC TATTTCCTAA GAGTCCTCCC TGTCCTCCAC TGCCCTCGGC
-1827 TCAGAGGCAT ACGGTCAAGG CAGTGGCTGG GGAACACTCC CTGAATGAGA TCAAGGAGGG
-1767 CTTGTTCACA GAGAAAGGGA GAATCCATTT GGGGAGCCTG AGAGTGACTC GAAGGCAAGG
-1707 ACTGGGCCTC ACCTGTGGGA TCTCCATCTG TGAGCATCCG CTCATCAGAC CAGTGTGAGA
-1647 TATTTTAAAT AAGGCCCCTA AGCCTCTTGA CTACTGGAAT TGCCAGGGGC GGGGGACAGA
-1587 TGGGCACCCA TCCCTATTTA ACAGATAACA AGACTGAGTC CAGAGAGGCA GTGCACCTGC
-1527 CCTGGTCTCT CTTAGTTCCT CAGCATCAGT GGAGCAGATT GGACACAGTG GGCCAGAAGG
-1467 GAAGCAGGCA GCCCTCCCTC CTAGCCCAAG CTACTCTGTG TAGTCAGTTT GCCCTCCTAC
-1407 TGGTGTTACA AGAAGCCTGT GGTATCCAAG AGGGCAGGTC AGAAAGCCCA CTGAGAGCAG
-1347 ACACTGTGTG TCACTTAGCT GGTTCTCAGG TGGCTGCCAC TTCCTGCTGC CTGTTGCAAA
-1287 ACTCGACACT AGGCCTTTAT AGATACTCAC GTGACCAGGA GTAAACAACC TTTCACCTCA
-1227 ATCACCTGCT CTTATCAATA CTCCCTCTCC ACCCCACCAT CGGGAAAGTT CAGACACCTT
-1167 AAAACGTAGA GGCAAGAGAG GGTCCATTCT GACACCTCAG CGACTTTCAG GCAGTGGCTG
-1107 AACCCGTTAC AACGCTCTGT GGACAGTCCT CCTAGTCGAC ATTCCTTCTC AGGTTTGACC
-1047 CTGTCCTGGG AAGTGAGGCT TCTCTCTCTG GGTTCCCCAC TCCTGTTCTT GAATAAGGAG
 -987 CCCCACAACC TCTTATTCTC TCTATACAGA GCCTGGGAAA CAGCAAAACT CGGCTCGCCT
 -927 ACAAGACTCC AGCGCGCCCT CTGGTGGACT CGGGGGACGA GCATGGGATG AGGGTTTCTT
 -867 TCCTCTAGCT CCCCCACCGC GCCGAGAGTA CCTGGGCGGA CCCACAGTTC GCCACGCAGG
 -807 TTGGGAGGCC CAGATGAGTG ATAAGGTAGT AGTTAGCTGC TCCTCCCACC CCACTCCCCA
 -747 AAGGACATCA GCACCCACGT CTGTCACCGA AGAACCAGGC AATGGGCGGA TGAGCTGAGG
 -687 CCAGGTAGCT GCTTCTAAGT CAGTGTCTCC TCCACTTCTG GATCTCACAG CTTCATCTTT
 -627 TGGACCTGTC TACAGGTAAA TGTCGCGCAT CCCCCTCCTC CACTTCCTAG GTCCCCAGTG
 -567 GGCTGGTGGC TGAATGGTCC TACGTCCCTT TTGGTTGGCA CGGGATGCTT GGAACTGTAC
 -507 ATGAGGACCT CGGGGTGGCC TGGGTGCAGA GGGAGGGGAG CGTCCCCGCG GGGATCAAAA
 -447 GAAAGGGAAG GGGTGCCAGG AGGGAGCCTC TCCCGGCTGG CCTCCTAGAA CTGCCCGCGC
 -387 GCTCCCATCG CGACGCCCCC GCCTCTGCCA GAAACCAGCC TTCTTAGAAG GGAGGGGGGG
 -327 GAAAGTGTGA ATGAGAAGTT GGGGGCGGAG CGCGCGGGGG AGGGGCCGCT GCCAGGAACG
 -267 CTCGGCCAAG GCTGGCGCCG CGCCCGCCGG TCGGGCAGCC TCGCGCCGCG CTTTGTCTCC
 -207 CTCTCGGTGA GTCTCGGCGG GTCCTGGAGG CCCCAGCTCC AAGCCCGCCC TCCGCAGCCC
 -147 CTCCCTCGCC CTCCGCGCAC AGCCTTTCAG TGCAGAGTAG TGACTAAACA TTACAAGAAG
  -87 ACCGGCCGGG CAGTTCCAGG AATCGGGGGG CGGGGCGTAC TGGCCGGGTA AATACCCGCG
```

-continued

```
 -27  CGCGCGGCCT CCGAGGCGGC TCTAACTCTG ACTCTACACT CGCCCGCTCC TACGACCGCT

+34  GTCTCTCCGG GCTCCCGGAC GCCCCCTTCC CGGCCCAGCT CTCCGTCGAG GTCCCTCGCC

+94  CAGGTCCTTT GCCTGATTCG CCCAGGAGTG CGCCTCATCG GCCCGGGGAG CAGCGAAGCC

+154  AGAGGGGGCG CACGCACGGG GAGCCCCTTT GTAGACTTCA CGGCTGCCAA CATCTGGGCG

+214  CAGCGCGAGC CACTGCTGGG CGCCGCCTCG CCTCGGGGAC CATAGGAGGC GCAGCCCCAA

+274  GGCCGGAGAT TTCGCT TCGG GACTAGGTAG GAAGGAGGGG CGCGGTGTGG GGAAGGGTGG

+334  GGGCATCGGT CCAGCTCGGG AGCTTTTCCC GGTTTCTCCT CCCCTTCCCG GGTCATTCCC

+394  GGTAGGGAGG GGACGAGGCA GGGGGCAGAG CGGATGAGAA CCGAAGATCC CTGATTCCCG

+454  TCATACTCAG ACTGGGGCCC TCGGGTTTCT CCTGTCCCCT CTCTCACATA TCTCGGGTTT

+514  GGCACCCCCC TTTTTTCGCC CTCGCCACTG AGGACACCGG ACTGAGAGGC GCCCTGAGCG

+574  TCCCTAGGGC TCTTGTGTCT CTCCCCATCC TGGCCGCGCT CCTGGAGACC CAACTTCCAC

+634  GCGCGAGTTT TCTCTGGGCG TCCTCCTAGG GCGGGCAGGG GAAGAGACTG TCTGGGGTTG

+694  GCCGGCAGTG ACCGAGGACA GTCGAGTTCC GCGAGGTGGC TGGGCCTGAG ACACGGTCTA

+754  AAGCGGGGCA AAGGGGTGCC CCGGGCGCTA GGCGGAGGCT GGAGGGCCGG GCACGCTGGA

+814  GGGTTCCGGG CACTCACGCG CCTCACGCTT TGCTCTCTGC AGCTCCCCGG GATGCGGTAG

+874  CGGCCGCTGT GCGGAGGCCG CGAAGCAGCT GCAGCCACCG CCGCGCAGAT CCACGCTGGC

+934  TCCGTGCGCC ATGGTCACCC ACAGCAAGTT TCCCGCCGCC GGGATGAGCC GCCCCCTGGA

+994  CACCAGCCTG CGCCTCAAGA CCTTCAGCTC CAAAAGCGAG//  (SEQ. ID. NO.:1)
```

A preferred embodiment of the SOCS-3 promoter of the present invention is a DNA fragment with the sequence of nt. −2907 to +1033, inclusive (SEQ. ID. NO.:1). Other preferred embodiments of the SOCS-3 promoter include any operative fragment of SEQ. ID. NO.: 1 or non-murine homologue thereof, or an operative derivative of any of these.

Preferred examples of an operative fragment include the −2759 to +104 fragment (SEQ. ID. NO.:2); the −2759 to +927 fragment (SEQ. ID. NO.:3); the −1864 to +927 fragment (SEQ. ID. NO.:4); the −857 to +927 fragment (SEQ. ID. NO.:5); the −63 to +927 fragment (SEQ. ID. NO.:6); the −97 to +927 fragment (SEQ. ID. NO.:7); the −97 to +104 fragment (SEQ. ID. NO.:8); the −87 to +927 fragment (SEQ. ID. NO.:9); the −87 to +104 fragment (SEQ. ID. NO.:10); and the −275 to +158 fragment (SEQ. ID. NO.:11). A most preferred example is the −161 to +927 fragment (SEQ. ID. NO.: 12).

Non-murine homologues include any SOCS-3 promoter sequence of non-murine origin that functions in a vertebrate cell type of interest.

Another preferred embodiment of a SOCS-3 promoter is an operative derivative of SEQ. ID. NO: 1, or of any operative fragment of SEQ. ID. NO.:1 or non-murine homologue thereof, having the translational start site (the ATG in bold at nt. +944 to +946 of the murine sequence above) changed to ATT, or changed to a codon sequence, other than ATT, that is also not recognized as a translational start site; another preferred SOCS-3 promoter is a derivative of SEQ. ID. NO.:1 with the codon of the first translational start site deleted altogether. Other operative derivatives include SOCS-3 promoter sequences containing a mutation, polymorphism, or variant allele with respect to any nucleotide position of SEQ. ID. NO.:1 that does not fully eliminate promoter activity, for example, a deletion of nt. −101 to −62, or a deletion of nt. −80 to −60, or a mutation of nt. −74 to −66. The skilled practitioner is aware of suitable methods for site-directed mutagenesis, e.g., the method of Deng and Nickoloff (W. P. Deng and J. A. Nickoloff, Analyt. Biochem.200:81–88 [1992]), and commercial site-directed mutagenesis kits are available, for example Transformer® site-directed mutagenesis kit (Clontech).

The murine SOCS-3 gene promoter contains a pair of STAT binding elements TT($N_5$)AA (SEQ. ID. NO.:31), separated by 14 nucleotides, at nt. −74 to −66 and at nt. −97 to −88. In this respect, the murine SOCS-3 promoter is structurally similar to the human CIS gene promoter, which contains two functionally important pairs of STAT binding elements and is upregulated by a STAT-5 dependent pathway. (A. Yoshimura et al. [1995]; A. Matsumoto et al. [1997]; F. Verdier et al., Mol. Cell. Biol. 18:5852–60 [1998]). However, for activity from the present SOCS-3 promoter, only the STAT binding element at −74 to −66 is essential for optimal operability.

In a preferred embodiment, the SOCS-3 promoter is operatively linked to a DNA having a DNA sequence encoding any preselected protein or series of preselected proteins. For purposes of the present invention, "operatively linked" means that the promoter sequence, is located directly upstream from the coding sequence and that both sequences are oriented in a 5' to 3' manner, forming a transcriptional unit, such that transcription could take place in vitro in the presence of all essential enzymes, transcription factors, co-factors, activators, and reactants, under favorable physical conditions, e.g., suitable pH and temperature. This does not mean that, in any particular cell, conditions will favor transcription.

These DNA sequence encoding a preselected protein(s), or a gene-specific part, are derived from the genome of any eukaryotic organism, prokaryotic organism, or virus, and can be autologous, allogeneic, or xenogeneic with respect to the host cell. DNA sequences having a "normal" form of a gene, or a desirable allele thereof are useful in genetic therapy to compensate for endogenous production of defective protein(s) or the underexpression or overexpression of normal protein(s). In some embodiments, natural variant alleles of a gene are used, or novel genetic modification(s) are artificially induced in the DNA sequence encoding the preselected protein. Variant alleles or mutations are not limited to single nucleotide polymorphisms (SNPs), but also include deletions, insertions, inversions, translocations, transitions, tranversions, or repeats. Mutations or variations are artificially induced in the DNA sequence encoding the preselected protein by a number of techniques, all of which are well known in the art. Alternatively, the DNA sequence linked to the SOCS-3 promoter encodes a gene-specific antisense RNA, such as an antisense RNA that specifically hybridizes to SOCS-3 mRNA, preventing translation therefrom. In another embodiment, the DNA sequence encodes a catalytic RNA, such as a "hairpin" or "hammerhead" ribozyme, that specifically hybridizes to a predetermined mRNA of interest and cleaves it, thereby preventing any further translation therefrom.

Most preferably, transcription of the DNA sequence from the SOCS-3 promoter results in RNA transcript that is biologically active in the cell or organism of interest, for example, as mRNA that is translated into functional protein (s); or as antisense RNA that specifically hybidizes with a functional mRNA of interest, for example a SOCS-3 mRNA, and thus prevents its translation to protein; or as catalytic RNA that specifically hybridizes with and cleaves a predetermined mRNA of interest.

In one embodiment, the preselected protein is a SOCS-3 protein, or a functional fragment thereof. Transcription of the DNA sequence encoding the SOCS-3 protein produces mRNA transcript, which is translated into SOCS-3 protein, or a functional fragment thereof. Thus one benefit of the present invention is that the nucleic acid can be used in a genetic therapy to correct clinical disorders derived from defective negative regulation of cytokine signal transduction in GH-responsive or gp130-responsive cells. Such defective negative regulation can result from, but need not result from, endogenous underexpression of functional SOCS-3 protein, which protein inhibits in an autocrine manner the cytokine-induced Jak-STAT cascade and SOCS-3 protein synthesis itself. But an unmodulated cellular response to GH and IL-6-type cytokine signaling caused by a defect in any of various components of the cellular signal transduction mechanism can also be negatively regulated using the present nucleic acid construct containing a DNA sequence encoding a SOCS-3 protein, or a functional fragment thereof.

In another embodiment, the DNA sequence operatively linked to the SOCS-3 promoter, encodes a SOCS-3-specific nucleotide sequence, transcription of which results in the production of RNA transcript in an antisense orientation that can hybridize to SOCS-3-encoding mRNA to prevent synthesis of SOCS-3 protein. In another embodiment, SOCS-3-specific sequences are included in a DNA sequence that encodes a catalytic RNA that specifically hybridizes to SOCS-3 mRNA. These embodiments are beneficially applied to genetic therapy to correct clinical disorders derived from negative overregulation of cytokine signal transduction in GH-responsive or gp130-responsive cells.

Other preferred embodiments of the present nucleic acid construct also include, operatively linked to the SOCS-3 promoter, a DNA sequence encoding a reporter protein for facilitating the detection or selection of cells containing the present nucleic acid construct and expressing from the SOCS-3 promoter. Preferably, but not necessarily, the reporter gene encodes a fluorescent protein. Fluorescent proteins include green fluorescent protein (or enhanced green fluorescent protein), yellow fluorescent protein, blue fluorescent protein, a phycobiliprotein, such as phycoerythrin or phycocyanin, or any other protein which fluoresces under suitable wave-lengths of light. Another reporter gene suitable for some applications is a gene encoding a protein that can enzymatically lead to the emission of light from a substrate(s); for purposes of the present invention, such a protein is a "light-emitting protein." For example, a light-emitting protein includes proteins such as luciferase or apoaequorin.

The DNA of animal cells is subject to methylation at the 5' carbon position of the cytidine bases of CpG dinucleotides. Unmethylated CpGs are found preferentially in transcriptionally active chromatin. (T. Naveh-Many et al., *Active gene sequences are undermethylated*, Proc. Natl. Acad. Sci. USA 78:4246–50 [1981]). Hypermethylation is associated with transcriptional repression. (R. Holliday, *The inheritance of epigenetic defects*, Science 238:163–70 [1987]). Since some vertebrate cell types of interest may silence expression from the present SOCS-3 promoter sequence by methylation, the skilled practitioner is aware that suitable insulator elements are employed to prevent methylation of the promoter sequence. Preferably, this is done by flanking the transcriptional unit of the promoter sequence and included gene(s) with insulator elements. For example, by including double copies of the 1.2 kb chicken β-globin insulator element 5' to the SOCS-3 promoter sequence and 3' to the operatively linked gene(s) in the present DNA construct, methylation will be substantially prevented at CG dinucleotide sites within the SOCS-3 promoter sequence and thus expression therefrom occurs. (M. J. Pikaart et al., *Loss of transcriptional activity of a transgene is accompanied by DNA methylation and histone deacetylation and is prevented by insulators*, Genes Dev. 12:2852–62 [1998]; Chung et al., *DNA sequence which acts as a chromatin insulator element to protect expressed genes from cis-acting regulatory sequences in mammalian cells*, U.S. Pat. No. 5,610,053).

The present invention also relates to a transgenic vertebrate cell containing the nucleic acid construct of the present invention, regardless of the method by which the construct was introduced into the cell. The present cell is a growth hormone (GH)-responsive or gp130-responsive cell, for example, a cell that specifically binds any IL-6-type cytokine (i.e., binds a cytokine of the gp130 signaling subunit cytokine family). Embodiments include pituitary cells, hypothalamic cells, adrenal cells, intestinal cells, kidney cells, liver cells (e.g., hepatocytes), immune-competent cells, or bone-forming cells, such as osteoblasts. In one embodiment, the present cell is a corticotroph cell, but the cell may also be an intestinal epithelial cell, a lymphocyte, a somatotroph, a lactotroph, or a gonadotroph cell. For some in vitro applications, for example with a wide variety of non-murine cells, inhibitors of histone deacetylation and DNA methylation, such as trichostatin A or sodium butyrate, can be included in the culture medium to prevent possible silencing of expression from the SOCS-3 promoter. (M. J. Pikaart et al. [1998]).

The transgenic cells of the present invention are detected, isolated or selected from non-transgenic cells with the aid of, for example, a flow-activated cell sorter (FACS), set at the appropriate wavelength(s). Alternatively, the transgenic cells are detected, isolated or selected manually from non-transgenic cells using conventional microscopic technology.

In particular applications involving a transgenic cell that expresses additional xenogeneic genes from any promoter, this expression may be linked to a reporter gene that encodes a different fluorescent or light-emitting protein from the reporter gene linked to the SOCS-3 promoter. Thus, multiple reporters fluorescing or emitting at different wavelengths can be chosen and cell selections based on the expression of multiple traits can be made.

The present invention also relates to transgenic non-human vertebrates comprising such cells, for example, non-human primates, mice, rats, rabbits, gerbils, hamsters, canines, felines or other non-human mammals. Other vertebrates include birds such as chickens, turkeys, ducks, ostriches, emus, geese, guinea fowl, doves, quail, rare and ornamental birds, and the like. Broadly speaking, a "transgenic" vertebrate is one that has had foreign DNA permanently introduced into its cells. The foreign gene(s) which (have) been introduced into the animal's cells is (are) called a "transgene(s)." The present invention is applicable to the production of transgenic vertebrates containing xenogeneic, i.e., exogenous, transgenic genetic material, or material from a different species, including biologically functional genetic material, in its native, undisturbed form. In other embodiments, the genetic material is "allogeneic" genetic material, obtained from different strains of the same species, for example, from animals having a "normal" form of a gene, or a desirable allele thereof.

Gene delivery is by any suitable method including in vivo and vitro gene delivery methods. (E.g., D. T. Curiel et al., U.S. Pat. Nos. 5,521,291 and 5,547,932). Typically, gene delivery involves exposing a cell to a gene delivery mixture that includes preselected genetic material together with an appropriate vector, mixed, for example, with an effective amount of lipid transfecting agent (lipofection). The amount of each component of the mixture is chosen so that gene delivery to a specific species of cell is optimized. Such optimization requires no more than routine experimentation. The ratio of DNA to lipid is broad, preferably about 1:1, although other proportions may also be utilized depending on the type of lipid agent and the DNA utilized. This proportion is not crucial. Other well known gene delivery methods include electroporation or chemical methods. (E.g., M. Ostresh, *No barriers to entry: transfection tools get biomolecules in the door*, The Scientist 13(11):21–23 (1999). "Transfecting agent", as utilized herein, means a composition of matter added to the genetic material for enhancing the uptake of exogenous DNA segment(s) into a vertebrate cell. The enhancement is measured relative to the uptake in the absence of the transfecting agent. Examples of transfecting agents include adenovirus-transferrin-polylysine-DNA complexes. These complexes generally augment the uptake of DNA into the cell and reduce its breakdown during its passage through the cytoplasm to the nucleus of the cell.

Other preferred transfecting agents include Lipofectin®, DMRIE C, Cellfectin® or Lipofectamine (Life Technologies), LipoTAXI (Stratagene), Superfect or Effectene (Qiagen). Although these are not as efficient gene delivery (or transfecting) agents as viral transfecting agents, they have the advantage that they facilitate stable integration of xenogeneic DNA sequence into the vertebrate genome, without size restrictions commonly associated with virus-derived transfecting agents. A virus, or transfecting fragment thereof, can be used to facilitate the delivery of the genetic material into the cell. Examples of suitable viruses include adenoviruses, adeno-associated viruses, retroviruses such as human immune-deficiency virus, other lentiviruses, such as Moloney murine leukemia virus and the retrovirus vector derived from Moloney virus called vesicular-stomatitis-virus-glycoprotein (VSV-G)-Moloney murine leukemia virus, mumps virus, and transfecting fragments of any of these viruses, and other viral DNA segments that facilitate the uptake of the desired DNA segment by, and release into, the cytoplasm of cells and mixtures thereof. All of the above viruses may require modification to render them non-pathogenic or less antigenic. Other known vector systems, however, are also useful.

The present invention also relates to a method of treating a growth retardation disorder in a human subject, especially in a child or adolescent. The method involves genetically modifying a GH-responsive or gp130-responsive cell of a human subject having a growth retardation disorder, typically resulting in short stature, such as, but not limited to, dwarfism, GH deficiency, gonadal dysgenesis, chondrodystrophy, bone-cartilage dysplasia, or an idiopathic condition of severe short stature. Typically, the cell is a pituitary, adrenal, hypothalamic, liver, immune-competent, or bone-forming cell that is responsive to a growth-inducing cytokine in a paracrine manner. Examples include hepatocyte, lymphocyte, lymphocyte, chondrocyte, corticotroph, somatotroph, lactotroph, or gonadotroph cells, or cells derived from a pituitary tumor, adrenal tumor, hypothalamic tumor, liver tumor, or bone tumor.

The cell(s) are genetically modified by any suitable method, in vivo or in vitro, for example by transfection or transduction, using a nucleic acid construct of the present invention, comprising a SOCS-3 promoter sequence, or operative fragment thereof, operatively linked, in a transcriptional unit, to a DNA sequence encoding an RNA that specifically hybridizes to a functional SOCS-3 mRNA, i.e., a SOCS-3-specific antisense RNA. In response to the presence of a growth-inducing cytokine, in vivo, the cell transcribes, from the transcriptional unit, RNA transcript that hybridizes to SOCS-3 mRNA, preventing translation therefrom. This RNA transcript can be an antisense RNA or a catalytic RNA (ribozyme) that cleave the SOCS-3 mRNA. As a consequence, the amount of SOCS-3 protein produced within the genetically modified cell(s) is reduced relative to unmodified cells of the same kind, and one or more symptoms of the growth retardation disorder in the human subject are thereby improved, due to a lessening of SOCS-3-mediated suppression of gp130-mediated signal transduction from growth-inducing cytokines, such as GH, within the genetically modified cell(s).

The present invention also relates to a method of treating a growth acceleration disorder in a human subject. The method involves genetically modifying a GH-responsive or gp130-responsive cell from a tissue of a human subject having a growth acceleration disorder, resulting in greater than normal enlargement of one or more parts of the body, such as, but not limited to, gigantism, acromegaly, Cushing's disease, or an idiopathic condition resulting in abnormal, non-edemic enlargement of bones, or facial or other soft tissue features. Typically, the cell is a pituitary, adrenal, hypothalamic, liver, immune-competent or bone-forming cell that is responsive to a growth-inducing cytokine in a paracrine manner. Examples include hepatocyte, lymphocyte, chondrocyte, corticotroph, somatotroph, lactotroph, or gonadotroph cells, or cells derived from a pituitary tumor, adrenal tumor, hypothalamic tumor, liver tumor, or bone tumor.

The cell(s) are genetically modified by any suitable method, in vivo or in vitro, for example by transfection or transduction, using a nucleic acid construct, in accordance with the present invention, comprising a SOCS-3 promoter sequence, or operative fragment thereof, operatively linked, in a transcriptional unit, to a DNA sequence encoding a SOCS-3 protein, or functional fragment thereof. In response to a growth-inducing hormone or cytokine, in vivo, SOCS-3 mRNA transcript is transcribed from the transcriptional unit, resulting in translation of SOCS-3 message to SOCS-3 protein. The amount of SOCS-3 protein produced is thereby enhanced in the genetically modified cell(s) in response to the presence of a growth-inducing cytokine, such as GH or a cytokine of the gp130 signaling subunit family, compared to the amount in unmodified cells of the same kind. The symptom(s) of the growth acceleration disorder in the subject are thereby improved, due to increased SOCS-3-mediated cytokine signal suppression within the genetically modified cell(s). Thus, for example, in pituitary corticotroph cells, ACTH secretion is suppressed by increased levels of SOCS-3, ultimately leading to less production of glucocorticoid hormones by the adrenals and ameliorating symptoms of Cushing's disease. Similarly, the effects of excess GH, as for example in acromegaly, are moderated in accordance with the present method.

The present invention also relates to a method of treating an autoimmune disease, immune disease, or inflammatory condition in a human subject. Such diseases or conditions include, but are not limited to, Crohn's disease, ulcerative colitis, multiple sclerosis, systemic lupus erythematosus, rheumatoid arthritis, Grave's disease, allergic or anaphylactic reactions, or neuroendocrinological responses to psychological or physical stress. The method involves genetically modifying a cell(s) from the subject that is gp130-responsive, i.e., responsive to at least one pro-inflammatory cytokine, such as IL-6, LIF, or any other pro-inflammatory cytokine for which signal transduction is gp130-mediated. Typically, the cell is a pituitary, adrenal, hypothalamic, liver, intestinal, nerve, kidney, immune-competent, or bone-forming cell that is responsive to a pro-inflammatory cytokine in a paracrine manner. Examples include hepatocyte, lymphocyte, chondrocyte, neuron, intestinal epithelial, corticotroph, somatotroph, lactotroph, or gonadotroph cells.

The cell(s) are genetically modified by any suitable method, in vivo or in vitro, for example by transfection or transduction, using a nucleic acid construct comprising a SOCS-3 promoter sequence, or an operative fragment thereof, operatively linked, in a transcriptional unit, to a DNA sequence encoding a SOCS-3 protein, or functional fragment thereof. In response to an inflammatory cytokine of the gp130 signaling subunit family, in vivo, SOCS-3 mRNA transcript is transcribed from the transcriptional unit, resulting in translation of SOCS-3 message to SOCS-3 protein. The amount of SOCS-3 protein produced is thereby enhanced in the genetically modified cell(s) in response to the presence of an inflammatory cytokine of the gp130 signaling subunit family, compared to the amount in unmodified cells of the same kind. One or more symptoms of the autoimmune disease, immune disease, or inflammatory condition in the subject are thereby improved, due to a relative increase in SOCS-3-mediated signal suppression.

In another embodiment, the nucleic acid construct that is used in the method comprises a SOCS-3 promoter sequence, or operative fragment thereof, operatively linked, in a transcriptional unit, to a DNA sequence encoding a functional anti-inflammatory cytokine of the gp130 signaling subunit cytokine family, such as IL-11, linked to a functional secretory signal. In response to the presence of a pro-inflammatory cytokine of the gp130 signaling subunit cytokine family, in vivo, the anti-inflammatory cytokine is produced and secreted by the modified cell(s), which has both paracrine and autocrine effects that improve One or more symptoms of the autoimmune disease, immune disease, or inflammatory condition in the subject.

In some embodiments of the present methods, gene delivery is done in vitro, and the cell(s) is first obtained from a tissue of the human subject by any suitable biopsy method, for example percutaneous biopsy, laparoscopic biopsy, or stereotactic cranial biopsy. Gene delivery is accomplished in vitro, and the genetically modified cell(s) are then re-implanted within the tissue of the human subject.

The nucleic acid construct that is used in the present methods optionally contains a reporter gene for convenient detection, isolation or selection of transgenic cells expressing from the SOCS-3 promoter as described herein. For particular applications, other DNA sequences encoding other preselected proteins are optionally linked to the SOCS-3 promoter, making their expression inducible by LL-6-type cytokines and gp130-mediated signal transduction.

The present invention also relates to a kit for genetically modifying a vertebrate cell. The kit is a ready assemblage of materials or components for facilitating the genetic modification of a vertebrate cell. The kit includes a polynucleotide comprising a murine SOCS-3 promoter sequence having SEQ. ID. NO.:1, or an operative fragment or non-murine homologue thereof, or an operative derivative of any of these, as described herein with respect to the nucleic acid construct of the present invention. Preferably the polynucleotide includes a transcriptional unit that contains the SOCS-3 promoter, operatively linked to at least one DNA sequence encoding a preselected protein or to a gene-specific part thereof, such as a SOCS-3 protein, or a functional fragment thereof, and/or a reporter gene for facilitating detection, isolation, or selection of genetically modified cells from unmodified cells. The DNA sequence encoding the preselected protein can be in a sense or antisense orientation as appropriate for a particular application. Some embodiments of the kit are configured for use in practicing the present methods of treating a growth retardation or acceleration disorder in a human subject or the present method of treating an autoimmune disease, immune disease, or inflammatory condition in a human subject.

The kit optionally contains a suitable transfecting agent, as described above. The kit includes instructions for using the materials or components effectively. The materials or components assembled in the kit are provided to the practitioner stored in any convenient and suitable way that preserves their operability and utility. For example the components can be in dissolved, dehydrated, or lyophilized form; they can be provided at room, refrigerated or frozen temperatures.

The foregoing descriptions of the nucleic acid constructs, transgenic cells, transgenic vertebrates, methods, and kits of the present invention are illustrative and by no means exhaustive. The invention will now be described in greater detail by reference to the following non-limiting examples.

EXAMPLES

Example 1

Materials and Methods

Materials. Recombinant murine LIF, IL-6, and IL-11 were purchased from R&D Systems (Minneapolis, Minn.). Mouse liver Marathon-Ready® cDNA, Advantage®-GC cDNA polymerase, mouse GenomeWalker® Kit, and Advantage®-GC genomic polymerase were from Clontech (Palo Alto, Calif.). Maxiscript® T7 polymerase kit and ribonuclease protection kit RPA-II® were from Ambion (Austin, Tex.). Polyclonal STAT-1 p84/p91 (M-22) and STAT-3 (H-190) antibodies were from Santa Cruz Biotechnology (Santa Cruz, Calif.). Mouse genomic DNA, Erase-a Base® system, pGL3 Basic and pSV-β-galactosidase vector were from Promega (Madison, Wis.). TOPO-TA® PCR2.1 vector was from Invitrogen (Carlsbad, Calif.).

Cell Culture. Cell culture of AtT-20/D16v-F2 cells was performed as described (C. J. Auernhammer et al. [1998b]; C. J. Auernhammer et al. [1998a]). Individual clones of AtT-20 cells, overexpressing SOCS-3 (AtT-20S), mock-transfected (AtT-20M), wild type STAT-3 (AtT-20W) or dominant negative STAT-3 mutants (AtT-20 F and AtT-20D), were isolated after stable transfection. (C. J. Auernhammer et al. [1998b]; C. Bousquet & S. Melmed, J. Biol. Chem. 274:10723–30 [1998]). From each group, three separate individual clones with high stable overexpression of the respective construct were selected with G418 (1 mg/mL) for the experiments.

Northern blot analysis. Northern blot analysis was performed as described (C. J. Auernhammer et al.[1998b]; C. J. Auernhammer et al. [1998a]). To detect endogenous SOCS-3 mRNA in AtT-20S cells, without hybridization to exogenous SOCS-3 mRNA derived from stable overexpression of SOCS-3, a probe spanning exon 1 and the untranslated 5' region of exon 2 as used. Otherwise, the previously described (C. J. Auernhammer et al. [1998b]; C. J. Auernhammer & S. Melmed, Endocrinology 140:1559 [1999]) murine SOCS-3 probe spanning most of the coding region of SOCS-3 was used.

5'-Rapid Amplification of cDNA Ends (RACE) and RNase protection Assay. 5'-RACE was performed with a pre-made, adaptor-ligated Marathon-Ready® double stranded cDNA derived from pooled BALB/c mouse liver (A. Chenchik et al., Biotechnol. 3: 526–34 [1996]) and Advantage®-GC cDNA polymerase using gene-specific primary and nested antisense primers 5'-CAGTAGAATC-CGCTCTCCTGCAGCTTG-3'(SEQ.ID.NO.:15) and 5'-CTCGCTTTTGGAGCTGAAGGTCTTGAG-3' (SEQ. ID. NO.:16). Products were cloned into PCR2.1 vector, and multiple single clones sequenced.

RNase protection assay was performed with RPA-II® kit, following the manufacturer's recommendations. A fragment spanning nucleotides +158 to −275 was cloned into PCR.2.1 vector; the plasmid was linearized with BamHI, and a $^{32}$P-UTP labeled antisense probe was generated with T7 polymerase.

PCR-based characterization of the 5'-genomic region. The 5'-genomic region of SOCS-3 was cloned using a PCR-based technique (P. D. Siebert et al., Nucleic Acids Res. 23:1087–88 [1995]) with pre-made adaptor-ligated genomic DNA fragments, derived from ICR Swiss mice, as provided by the Genomewalk® kit. PCR and subsequent nested PCR where performed by automatic hot-start as touchdown-PCR using Advantage®-GC genomic Polymerase and gene specific antisense primers 5'-CAGTAGAATCCGCTCTCCTG-CAGCTTG-3' (SEQ. ID. NO.:15) and 5'-CTCGCTTTTG-GAGCTGAAGGTCTTGAG-3'(SEQ.ID.NO.:16). Further genomic walks in the 5' direction were performed with gene specific antisense primers 5'-CTTCCTACCTAGTC-CCGAAGCGAAATC-3'(SEQ.ID.NO.:17), 5'-CAGATGT-TGGCAGCCGTGAAGTCTAC-3'(SEQ.ID.NO.:18), 5'-GCGGGCGAGTGTAGAGTCAGAGTTAGAG-3'(SEQ.ID.NO.:19), and 5'-CGATTCCTGGAACTGCCCGGC-CGGTCTTC-3'(SEQ.ID.NO.:20), as well as 5'-CT-CAGTGGGCTTTCTGACCTGCCCTCTTG-3'(SEQ.ID.NO.:21) and 5'-GACTACACAGAGTAGCTTGGGCTAGGAG-3'(SEQ.ID.NO.:22). Products were cloned into PCR2.1, and single clones were sequenced.

Different Constructs of the 5' Genomic Region of SOCS-3. 3'-Truncated forms of the full-length 3.7-kb construct in pGL3Basic vector (clone 6) were generated by PCR from genomic DNA and subsequent cloning as described above.

5'-Truncated forms of clone 6 were generated using Erase-a-Base® kit, following the manufacturer's recommendations. Briefly, the 3.7-kb full-length construct of the 5' genomic region of SOCS-3 in pGL3Basic vector was digested with SstI and NheI, followed by unidirectional digestion with exonuclease III (S. Henikoff, Gene 28:351–59 [1984]) and subsequent re-ligation.

Mutated forms of clone 6 were generated by overlap extension PCR (A. Aiyar et al., Methods Mol. Biol. 57:177–91 [1996]) with Pfu polymerase and 5% DMSO, by using external sense primer 5'-CATCGCGACGCCCCCGC-CTCT-3' (SEQ.ID.NO.:23) and antisense primer 5'-GAAACCCGAGGGCCCCAGTCTG-3'(SEQ.ID.NO.:24) with exclusive restriction sites for NruI or ApaI, respectively. Internal mutagenizing primers caused deletions of nucleotides −80 to −60 and −101 to −62, respectively. Similarly, the STAT binding element region at −74 to −66 was mutated. Gel-purified PCR-products and the original template were digested with NruI and ApaI, fragments were purified, and the mutated fragments were re-ligated into the original 3.7-kb construct in pGL3Basic vector. Each construct was verified by sequencing.

Luciferase Assay. For transient transfection experiments, $2 \times 10^5$ cells were plated in 6-well plates, incubated for 24 hours, and transfected using Lipofectamine-re and 0.5 μg of constructs in pGL3Basic vector, and 1.0 μg pSV-β-galactosidase. Transfected cells were first incubated for 24 hours in serum-free DMEM, followed by 6 hours of cytokine treatment and subsequent measurement of luciferase activity. In experiments comparing overexpressing dominant negative STAT-3 mutants or wild type SOCS-3, treatment with LIF was for 45 minutes.

In experiments using different promoter constructs, transfection efficiency was verified by measurement of β-galactosidase activity.

Electromobility shift assay. Nuclear extracts of AtT-20 cells and electromobility shift assay (EMSA) were performed as described (P. D. Siebert et al., Nucleic Acids Res. 23:1087–88 [1995]). Briefly, AtT-20 cells were grown to 80% confluence and were serum-deprived for 24 hours before treatment with $10^{-9}$ M LIF, followed by cell lysis and preparation of nuclear extracts. For the EMSA, 20-μg nuclear extracts were preincubated for 15 minutes at room temperature in 20 μL binding, buffer (10 mM Tris-HCl, 50 mM NaCl, 1 mM EDTA, 1 mM DTT, 0.1% NP-40, 5% glycerol, 1 mg/mL BSA, pH 7.5) with 1 μg of poly(dI-dC). A $^{32}$P-labeled double stranded oligonucleotide, corresponding to nucleotide sequence −77 to −57 of the SOCS-3 promoter (5'-$^{-77}$CAGTTCCAGGAATCGGGGGGC$^{-57}$-3)(SEQ.ID.NO.:25), was used as a probe (60,000 cpm, 5 fmol per reaction) and added to each sample and binding reaction, performed at room temperature for 20 min. In competition experiments, 100-fold molar excess of unlabeled double stranded competitor oligonucleotides were added to the preincubation reaction with the double stranded oligonucleotide corresponding to nucleotide sequence −77 to −57 of the SOCS-3 promoter, this same oligonucleotide mutated at positions −74, −71, −69, and −66 (underlined) (5'-$^{-77}$CAG<u>A</u>TC<u>GA</u>CGA<u>TT</u>CGGGGGGC$^{-57}$-3)(SEQ.ID.NO.:26), or the AP-2 recognition site oligonucleotide 5'-GATCGAACTGACCGC-CCGCCGCCCGT-3' (SEQ. ID. NO.:27). For supershift experiments 2 μg polyclonal STAT-1 p84/p91 or STAT-3 antibody was added to the preincubation reaction and incubated for an additional 60 min at 4° C. Protein-DNA complexes were run on a 6% non-denaturing polyacrylamide gel in 0.5× TBE buffer (90 mM Tris, 64.6 mM boric acid, 2.5 mM EDTA); gels were dried and autoradiographs were exposed (Kodak biomax MS film at −70° C.).

Statistical analysis. Statistical analysis was performed by unpaired t-test. All values are mean±SEM.

Example 2

5'-Genomic Sequence of Murine SOCS-3 and Determination of the Transcription Start Site by 5'-RACE and RNase Protection Assay Based on the sequence information from the 5' genome walk, a full length 5' product of murine SOCS-3 spanning ~3.8-kb of genomic sequence was generated from ICR Swiss mice genomic DNA by PCR with Advantage®-GC genomic polymerase using the following sense and antisense primers:

5'-GACGTTCCTAAAAGCATGCATGTCACC CAG-3' (SEQ.ID.NO.:28) and

5'-GGATCTGCGCGGCGGTGGCTGCAGCTGCTT-3' (SEQ.ID.NO.:29). Cloning of the product into PCR2.1 vector was followed by verification of sense orientation, sequencing, restriction enzyme digestion with SstI and XhoI, and subcloning of a ~3.7-kb construct into pGL3Basic vector (clone 6). Sequence information was obtained for the whole 3.8 kb. (SEQ. ID. NO.:1).

5'-RACE revealed the existence of an untranslated exon 1 (+1 to +289, SEQ. ID. NO.:32), separated from exon 2 (starting at +854; partial exon 2, sequence +854 to +1033 [SEQ. ID. NO.:34]) by an intron (+290 to +853; SEQ. ID. NO.:33). Using Rnase protection assay, the main transcription start site was defined and is referred to as +1. The previously determined translation initiation site for murine SOCS-3 (GenBank Accession U88328) (R. Starr et al., Nature 387:917–21 [1997]) was in exon 2 at +944.

Example 3

Effects of Different Cytokines on SOCS-3 Promoter Activity and Gene Expression

FIG. 1 shows the stimulatory effect of various cytokines on expression from the SOCS-3 promoter sequence. AtT-20 cells were either untreated, or stimulated with $0.5 \times 10^{-9}$ M LIF, IL-6, or IL-11 for 60 or 120 min. Northern blot analysis showed a SOCS-3-specific signal of uniform transcript size of ~2.8 kb (FIG. 1A).

LIF was the most potent inducer of SOCS-3 mRNA expression. Although IL-6 and IL-11 were less potent stimuli of SOCS-3 gene expression, they each showed a similar pattern of SOCS-3 mRNA induction. (FIG. 1A).

Figure 1B:
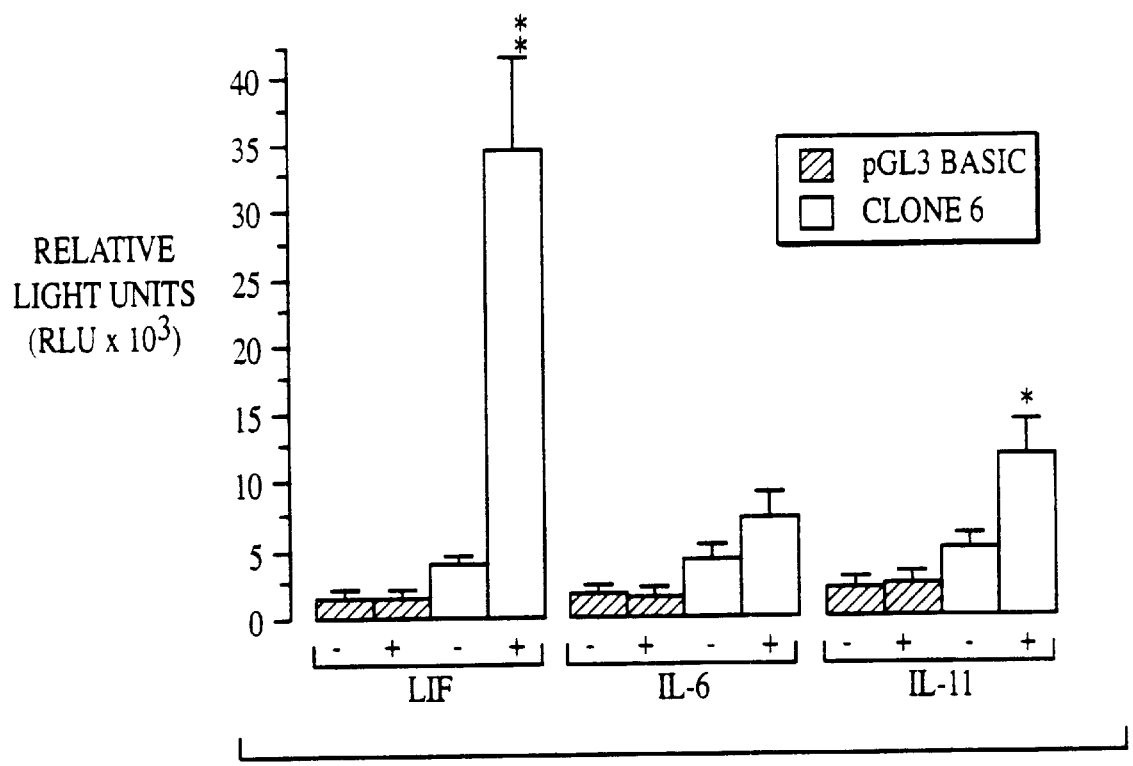
FIG. 1B shows luciferase activity in AtT-20 cells transfected with pGL3Basic alone or a −2757/+929 murine SOCS-3 promoter-pGL3Basic construct (clone 6).

For measurement of SOCS-3 promoter activity, transient transfections of AtT-20 cells were performed either with pGLBasic alone or with clone 6, a construct containing nucleotides −2,759 to +927 of the 5'-genomic region of murine SOCS-3 linked to the luciferase reporter gene in pGL3Basic vector. (FIG. 1B). Relative SOCS-3 promoter activity is indicated by relative light unit values in FIG. 1B, calculated from 4 independently performed experiments. Each experiment was performed with n=3 wells per group. Asterisks indicate in-group significance of untreated (−) vs. treated (+); *, P<0.05: **, P<0.01. AtT-20 cells transfected with clone 6 showed a significantly higher basal luciferase activity than cells transfected with pGL3Basic alone (4043±443 vs. 1611±398 relative light units [RLU]; P<0.001). Stimulation with $0.5 \times 10^{-9}$ M LIF, IL-6, or IL-11 caused no further increase of luciferase activity in control AtT-20 cells transfected with pGL3Basic alone. However, in comparison to untreated cells, AtT-20 cells transfected with clone 6 showed an approximately 10-fold (P<0.0 1) increase in luciferase activity following stimulation with LIF, a 2-fold (not significant) increase following stimulation with IL-6, and a 3-fold (P<0.05) stimulation of luciferase activity by IL-11. (FIG. 1B).

Activation by LIF, IL-6 and IL-11, of SOCS-3 promoter activity and gene expression thus is concordant with our finding of a functionally important STAT-1/STAT-3 binding element in the murine SOCS-3 promoter region.

Example 4

Figure 2A:
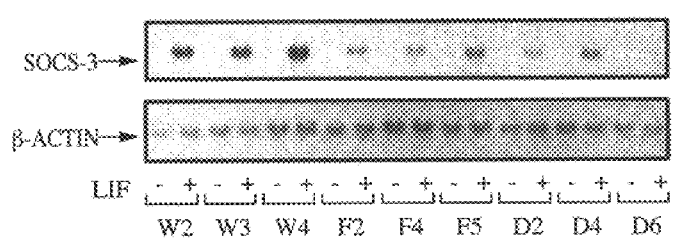
FIGS. 2A and 2D show Northern blot analysis performed with 15 μg total RNA per lane for a representative experiment; upper panel shows SOCS-3 mRNA; lower panel shows β-actin mRNA.
Figure 2D:
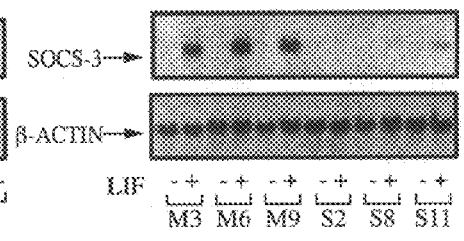
Figure 2C:
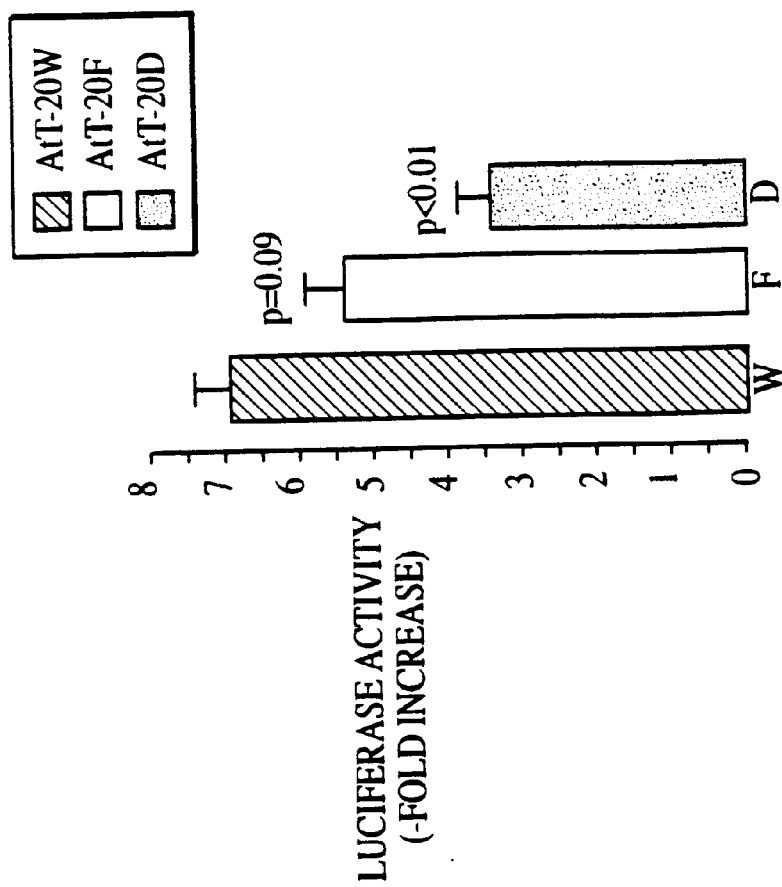
FIGS. 2C and 2F show relative luciferase activity in various cell clones bearing a −2759/+927 murine SOCS-3 promoter-pGL3Basic construct (clone 6).
Figure 2B:
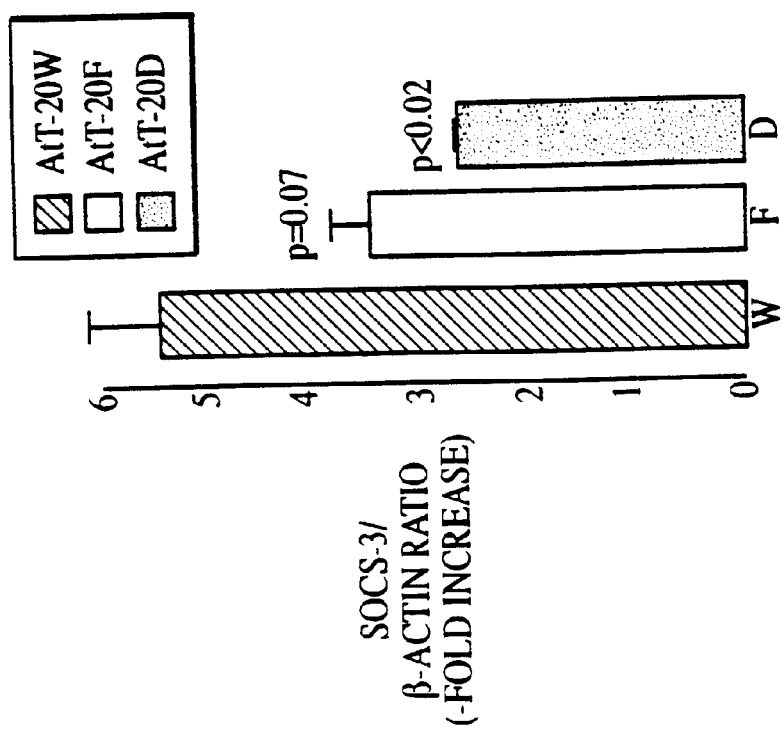
FIGS. 2B and 2E show Northern blot signals for SOCS-3 mRNA analyzed by quantitative densitometry and normalized for β-actin mRNA.

Effect of Overexpressed Dominant Negative STAT-3 Mutants or Wild Type SOCS-3 on LIF-induced SOCS-3 Gene Expression and Promoter Activity Expression from the SOCS-3 promoter is partly dependent both on the expression of STAT-3 and SOCS-3 itself. FIG. 2 shows the effect of overexpressed dominant negative STAT-3 mutant or wild type SOCS-3 on LIF-induced SOCS-3 gene expression and promoter activity in AtT-20 cells. AtT-20 cells overexpressing wild type STAT-3 (AtT-20W) showed a 5.4±0.7-fold increase of SOCS-3 mRNA levels after stimulation with $0.5 \times 10^{-9}$ M LIF for 45 min. In comparison, AtT-20 cells overexpressing the dominant negative mutants STAT-3F (AtT-20F) and STAT-3D (AtT-20D) both showed relatively diminished induction of SOCS-3 mRNA after stimulation with LIF: 3.4±0.4 (p=0.07) and 2.6±0.1-fold (p<0.02), respectively. (FIGS. 2A, 2B). Similarly, transient transfection experiments with clone 6 showed stimulation of luciferase activity by LIF (6.9±0.5-fold) in AtT-20W cells, but only 5.4±0.5-(P=0.09) and 3.4±0.4-fold (P<0.01) stimulation were observed in AtT-20F and AtT-20D cells, respectively. (FIG. 2C). These results, showing that LIF-induced SOCS-3 promoter activity and gene expression is decreased in these dominant negative STAT-3 mutant transfectants, indicate that SOCS-3 promoter activity is at least partly dependent on wild type STAT-3 expression. (FIGS. 2A–C).

Figure 2F:
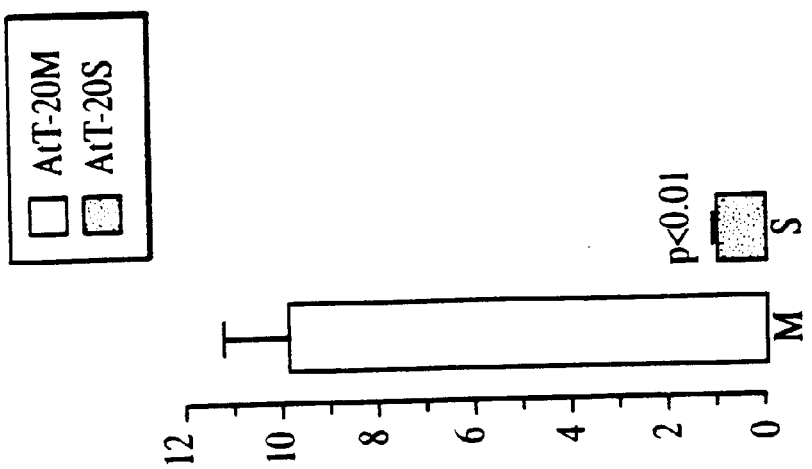
Figure 2E:
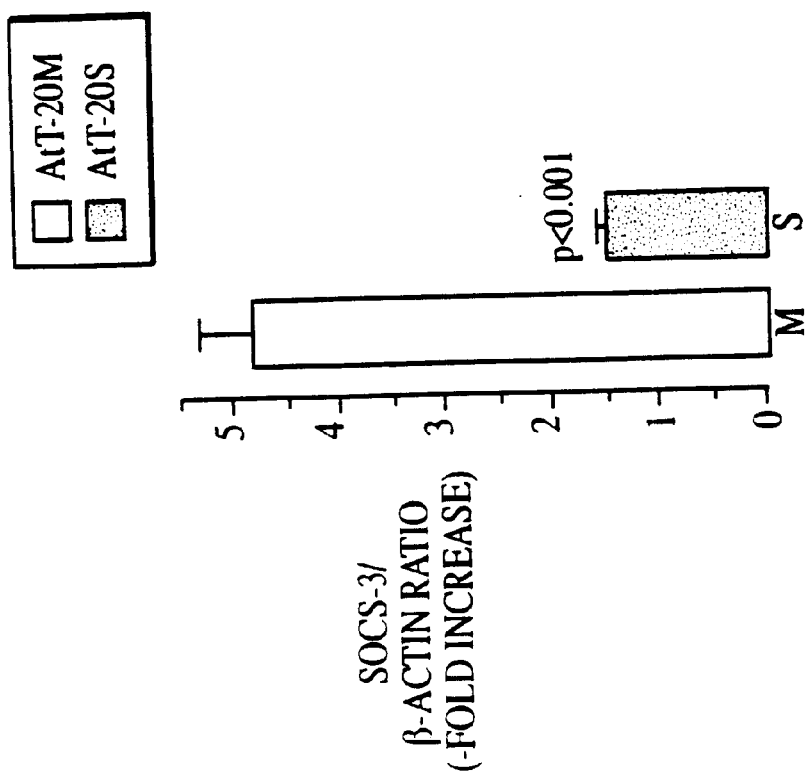

Overexpression of wild type SOCS-3 in AtT-20 cells abrogated LIF-induced SOCS-3 promoter activity and gene expression. (FIGS. 2D–F). Mock-transfected AtT-20 cells (AtT-20M) showed an approximately 5-fold increase of SOCS-3 mRNA levels after 45 min stimulation with $0.5 \times 10^{-9}$ M LIF, while AtT-20 cells overexpressing wild type SOCS-3 (AtT-20S), showed a significant inhibition of LIF-induced SOCS-3 mRNA expression. (FIGS. 2D, 2E). Similarly, transient transfection experiments with clone 6 revealed luciferase activity to be stimulated by LIF (9.9±1.3-fold) in AtT-20M cells, while LIF-induced luciferase activity in AtT-20S cells was abrogated and did not differ substantially from luciferase activity in untreated AtT-20S cells. (FIG. 2F). These results indicate a negative autoregulatory feedback of SOCS-3 on its own cytokine-induced gene expression.

LIF-induced SOCS-3 mRNA and luciferase activity were each calculated from 3 independently performed experiments. Each experiment was performed with 3 different clones per group. LIF-induced luciferase activity was normalized to the untreated control for each clone.

Example 5

Functional Analysis of Different SOCS-3 5' Region-luciferase Constructs

Clone 6 (SEQ.ID.NO.:3) is the −2759 to +927 5' genomic region of murine SOCS-3 linked to the luciferase reporter in pGL3Basic vector. 3'-Truncations of clone 6 were: clone 4 (nt. −2759 to +104; SEQ.ID.NO.:2) and clone 2 (nt. −2759 to −716; SEQ.ID.NO.:38). 5'-Truncations of clone 6 were: clone 6T1 (nt. −1864 to +927; SEQ.ID.NO.:4); clone 6T2 (nt. −857 to +927; SEQ.ID.NO.:5); clone 6T3 (nt. −152 to +927; SEQ.ID.NO.: 12); and clone 6T4 (nt. −63 to +927; SEQ.ID.NO.:6). Analysis of clone 6 sequence with Mat Inspector V2.2 (K. Quandt et al., Nucleic Acids Res. 23: 4878–84 [1995]), revealed potential STAT binding sites containing the consensus binding sequence TT(N)$_5$AA (SEQ. ID. NO.:31) (C. M. Horvath et al., Genes Dev.

9:984–94 [1995]; J. E. Darnell, Jr., Science 277:1630–35 [1997]; S. Becker et al., Nature 394:145–51 [1998]) located at nt. −97 to −89 and nt. −74 to −66, as well as at nt. −347 to −339 and −1403 to −1395. However, only the STAT binding site from nt. −74 to −66 showed the more specific sequence TTCCAGGAA (SEQ.ID.NO.:13), indicating a potential binding site for STAT-1 and STAT-3.

Therefore, in subsequent experiments, the focus centered on the STAT binding site at nt. −74 to −66, constituting part of the tandem STAT binding region pair of nt. −97 to −89 and nt. −74 to −66. Using overlap extension PCR, we deleted the complete tandem STAT binding region from nt. −101 to −62 (clone 6D2; SEQ.ID.NO.:36), or only the 3'-located STAT binding element from nt. −80 to −60 (clone 6D1; SEQ.ID.NO.:35). In clone 6M1 (SEQ.ID.NO.:37), the 3'-located STAT binding element from nt. −74 to −66 was not deleted, but mutated to ATCGACGAT, thus destroying the specific binding sequence TTCCAGGAA (SEQ.ID.NO.:13). Clone 8 (SEQ.ID.NO.:39) was a minimal −275 to +158 5' genomic region of SOCS-3 linked to the luciferase reporter in pGL3Basic vector. Basal and LIF-induced luciferase activity were assayed after transient transfection of corticotroph AtT-20 cells with the different constructs.

Figure 3:
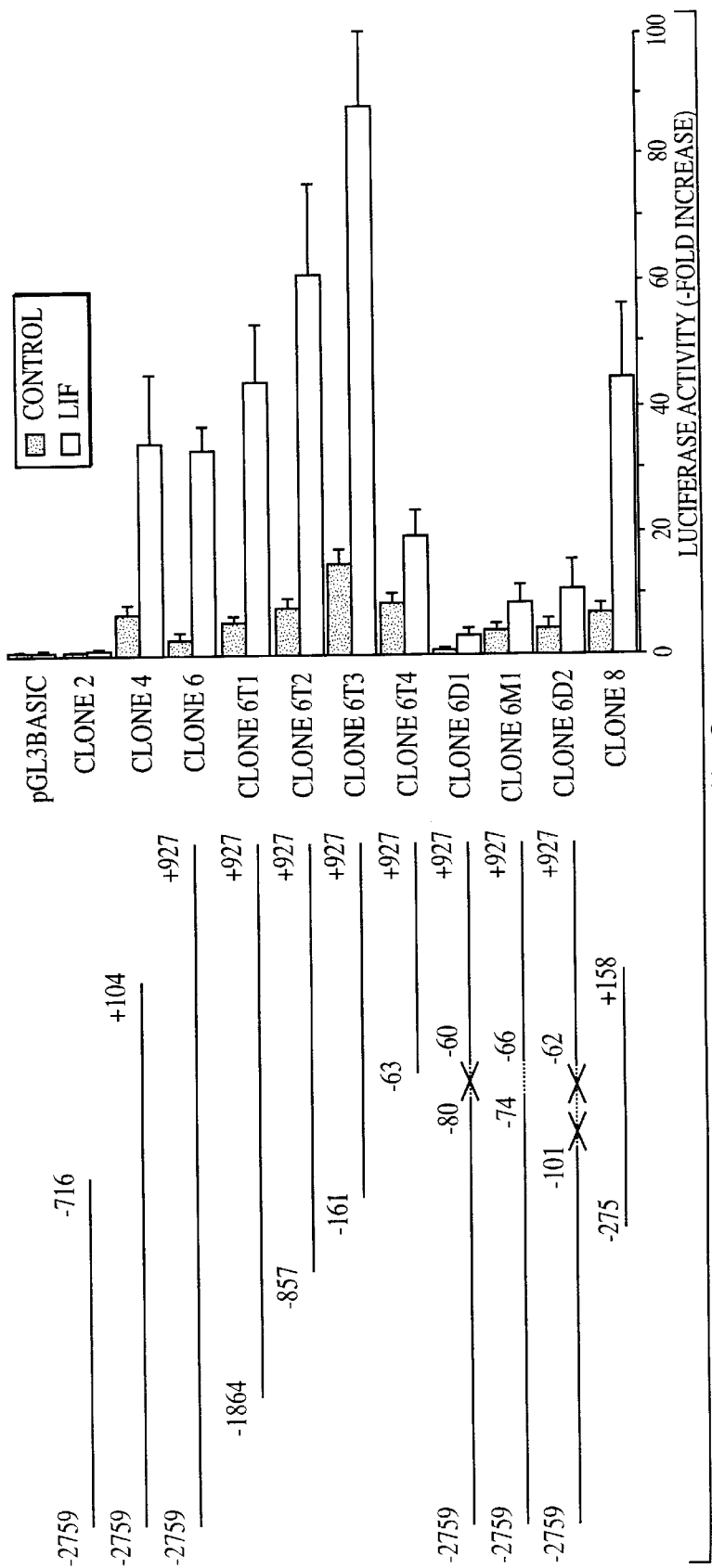
FIG. 3 shows relative luciferase activities in transiently transfected AtT-20 cells bearing different constructs of the genomic 5'-region of murine SOCS-3. Luciferase activity was measured in untreated (filled bars) and LIF-stimulated (unfilled bars) AtT-20 cells. Crossed lines indicate a deletion of STAT binding elements in Clone 6D1 (SEQ.ID.NO.:35) and 6D2 (SEQ.ID.NO.:36), in between the named nucleotides. A dotted line indicates a mutation of the wild type STAT binding sequence (5'-TTCCAGGAA-3'; SEQ. ID. NO:13) with mutant (5'-ATCGACGAT-3'; SEQ. ID. NO.:14) in clone 6M1 (SEQ.ID.NO.:37). Clone 2 corresponds to SEQ.ID.NO.:38; Clone 4 corresponds to SEQ.ID.NO.:2; Clone 6 corresponds to SEQ.ID.NO.:3; Clone 6T1 corresponds to SEQ.ID.NO.:4; Clone 6T2 corresponds to SEQ.ID.NO.:5; Clone 6T3 corresponds to SEQ.ID.NO.:12; Clone 6T4 corresponds to SEQ.ID.NO.:6; and Clone 8 corresponds to SEQ.ID.NO.:39. The nucleotide sequence at the top of FIG. 3, marked as −101 through −62, corresponds with nucleotide positions 2807 through 2846 of SEQ.ID.NO.: 1.

FIG. 3 shows relative luciferase activities in transfected AtT-20 cells bearing the different constructs. Relative luciferase activities were calculated in comparison to basal luciferase activity of pGL3Basic alone without LIF treatment, which was defined as 1.0. Basal luciferase activity of clone 2 (SEQ.ID.NO.:38) did not differ from pGL3Basic, and neither clone 2 (SEQ.ID.NO.:38) nor pGL3Basic showed induction of luciferase activity by LIF. However, clones 4 and 6 (SEQ.ID.NOS.:2 and 3, respectively) showed 7- and 4-fold higher basal luciferase activity, respectively, as well as 35-fold higher LIF-stimulated luciferase activity, compared to the pGL3Basic (P<0.01). This indicates that the region from nt. +104 to +927 is not involved in SOCS-3 promoter activity.

Increasing 5'-truncations of clone 6 up to nt. −161 caused a gradual increase of basal and LIF-stimulated luciferase activity, with both clone 6T2 (P<0.01) and clone 6T3 (P<0.001) showing significantly higher basal and LIF-induced luciferase activities than clone 6. Clone 6T3 had the highest basal (17-fold elevation) and LIF-induced (97-fold elevation) luciferase activities, compared to basal pGL3Basic (p<0.001). This demonstrates that the region from nt. −2759 to −161 contains apparent negative regulator elements, but is not responsible for basal and LIF-induced SOCS-3 promoter activity.

Further 5'-truncation to nt. −63 in clone 6T4 (SEQ.ID.NO.:6) caused decreases in basal activity and, more markedly, in LIF-inducible promoter activity. Mutated clones 6D1 (SEQ.ID.NO.:35) (P<0.001) and 6M1 (SEQ.ID.NO.:37) (P<0.01) showed reduced LIF-induced luciferase activity, compared to wild type clone 6 (SEQ.ID.NO.:3). (FIG. 3). Extending the deletion to the entire tandem STAT binding region in clone 6D2 (SEQ.ID.NO.:36), showed no significant difference in the magnitude of basal vs. LIF-induced luciferase activity in comparison to clone 6D1 (SEQ.ID.NO.:35). These results indicate that the specific STAT-1/STAT-3 binding element at −74 to −66 (TTCCAGGAA; SEQ.ID.NO.:13) mediates the LIF-induced rise in luciferase activity, while the more 5'-located STAT binding element at −97 to −89 (TTACAAGAA; SEQ.ID.NO.:30) does not significantly participate in this signal.

Clone 8 (SEQ.ID.NO.:39) showed basal and LIF-induced luciferase activity comparable to clone 6 (SEQ.ID.NO.:3). (FIG. 3). This further demonstrates the functional importance for SOCS-3 promoter activity of the region containing the STAT-1/STAT-3 binding element.

Example 6

Electromobility Shift Assay

EMSA showed specific binding of nuclear extracts from LIF-induced AtT-20 cells to a double stranded oligonucleotide probe spanning nt. −77 to −57 (STAT oligoprobe), including the STAT-1/STAT-3 binding element from −74 to −66. While nuclear extracts from unstimulated AtT-20 cells did not form specific complexes with the oligoprobe, nuclear extracts from LIF-stimulated AtT-20 cells formed three specific complexes, compatible with STAT-3 homodimers, STAT-1/STAT-3 heterodimers and STAT-1 homodimers (C. M. Horvath et al., Genes Dev. 9:984–94 [1995]; J. E. Darnell, Jr., Science 277:1630–35 [1997]; S. Becker et al., Nature 394:145–51 [1998]). The three complexes disappeared during self-competition with a 100-fold excess of unlabeled double stranded STAT oligonucleotide, whereas the same double stranded oligonucleotide mutated at positions −74, −71, −69, and −66, or a nonspecific double stranded AP-2 oligonucleotide had no effect. Incubation with a specific antibody directed against STAT-1 abolished the two bands representing STAT-1 homodimer and STAT1/STAT3 heterodimer. Similarly, incubation with a specific antibody directed against STAT-3 abolished the two bands representing STAT-3 homodimer and STAT1/STAT3 heterodimer. These results are evidence of specific binding of STAT-1 and STAT-3 to the SOCS-3 promoter region between nt. −74 to −66.

The foregoing examples being illustrative but not an exhaustive description of the embodiments of the present invention, the following claims are presented.

We claim:

1. A nucleic acid construct, comprising a murine SOCS-3 promoter having a nucleotide sequence SEQ ID NO: 1, or an operative fragment of SEQ ID NO: 1 having promoter activity that is inducible by LIF, IL-6, and IL-11.

2. The nucleic acid construct of claim 1, further comprising said SOCS-3 promoter operatively linked, in a transcriptional unit, to a DNA sequence encoding a protein of interest.

3. The nucleic acid construct of claim 2, wherein the protein of interest is a SOCS-3 protein, or a functional fragment thereof.

4. The nucleic acid construct of claim 2, wherein said SOCS-3 promoter is operatively linked to a DNA sequence encoding a reporter protein.

5. The nucleic acid construct of claim 4, wherein the reporter protein is a fluorescent or light-emitting protein.

6. The nucleic acid construct of claim 5, wherein the encoded fluorescent or light-emitting protein is a green fluorescent protein, yellow fluorescent protein, blue fluorescent protein, phycobiliprotein, luciferase, or apoaequorin.

7. The nucleic acid construct of claim 2, further comprising at least one insulator element flanking said transcriptional unit.

8. The nucleic acid construct of claim 7, wherein said at least one insulator element is a chicken β-globin insulator element.

9. A kit for genetically modifying a vertebrate cell, containing a polynucleotide comprising a murine SOCS-3 promoter sequence having a nucleotide sequence SEQ ID NO: 1, or an operative fragment of SEQ ID NO: 1 having promoter activity that is inducible by LIF, IL-6, and IL-11, and a suitable storage means for said polynucleotide.

10. The kit of claim 9, further comprising said SOCS-3 promoter operatively linked, in a transcriptional unit, to a DNA sequence encoding a protein of interest.

11. The kit of claim 10, wherein the protein of interest is a SOCS-3 protein, or a functional fragment thereof.

12. The kit of claim 10, wherein said SOCS-3 promoter is operatively linked to a DNA sequence encoding a reporter protein.

13. The kit of claim 12, wherein the encoded reporter protein is a fluorescent or light-emitting protein.

14. The kit of claim 13, wherein the encoded fluorescent or light-emitting protein is a green fluorescent protein, yellow fluorescent protein, blue fluorescent protein, phycobiliprotein, luciferase, or apoaequorin.

15. The kit of claim 10, wherein said polynucleotide further comprises at least one insulator element flanking said transcriptional unit.

16. The kit of claim 15, wherein said at least one insulator element is a chicken β-globin insulator element.

17. The kit of claim 9, further comprising a transfecting agent.

18. The kit of claim 17, wherein the transfecting agent is a liposome, viral vector, transferrin-polylysine enhanced viral vector, retroviral vector, lentiviral vector, or uptake enhancing DNA segment, or a mixture of any of these.

19. The kit of claim 17, wherein the transfecting agent comprises a retroviral vector, adenoviral vector, transferrin-polylysine enhanced adenoviral vector, human immunodeficiency virus vector, lentiviral vector, Moloney murine leukemia virus-derived vector, mumps vector, a DNA segment that facilitates polynucleotide uptake by and release into the cytoplasm of vertebrate cells, or comprises an operative fragment of or mixture of any of these.

20. The kit of claim 17, wherein the transfecting agent comprises an adenovirus vector having endosomal lytic activity, and the polynucleotide is operatively linked to the vector.

21. The kit of claim 17, wherein the transfecting agent comprises a lipid transfecting agent.

22. A nucleic acid construct, comprising a murine SOCS-3 promoter having a nucleotide sequence (SEQ ID NO: 1), (SEQ ID NO: 2), (SEQ ID NO: 3), (SEQ ID NO: 4), (SEQ ID NO: 5), (SEQ ID NO: 6), (SEQ ID NO: 7), (SEQ ID NO: 8), (SEQ ID NO: 9), (SEQ ID NO: 10), (SEQ ID NO: 11), (SEQ ID NO: 12), (SEQ ID NO: 35), (SEQ ID NO: 36), (SEQ ID NO: 37), or (SEQ ID NO: 39).

23. The nucleic acid construct of claim 22, further comprising said SOCS-3 promoter operatively linked, in a transcriptional unit, to a DNA sequence encoding a protein of interest.

24. The nucleic acid construct of claim 23, wherein the protein of interest is a SOCS-3 protein.

25. The nucleic acid construct of claim 23, wherein said SOCS-3 promoter is operatively linked to a DNA sequence encoding a reporter protein.

26. The nucleic acid construct of claim 25, wherein the reporter protein is a fluorescent or light-emitting protein.

27. The nucleic acid construct of claim 26, wherein the encoded fluorescent or light-emitting protein is a green fluorescent protein, yellow fluorescent protein, blue fluorescent protein, phycobiliprotein, luciferase, or apoaequorin.

28. The nucleic acid construct of claim 23, further comprising at least one insulator element flanking said transcriptional unit.

29. The nucleic acid construct of claim 28, wherein said at least one insulator element is a chicken β-globin insulator element.

30. A kit for genetically modifying a vertebrate cell, containing a polynucleotide comprising a murine SOCS-3 promoter sequence having a nucleotide sequence SEQ ID NO: 1, (SEQ ID NO: 2), (SEQ ID NO: 3), (SEQ ID NO: 4), (SEQ ID NO: 5), (SEQ ID NO: 6), (SEQ ID NO: 7), (SEQ ID NO: 8), (SEQ ID NO: 9), (SEQ ID NO: 10), (SEQ ID NO: 11), or (SEQ ID NO: 12), (SEQ ID NO: 35), (SEQ ID NO: 36), (SEQ ID NO 37), or (SEQ ID NO: 39), and a suitable storage means for said polynucleotide.

31. The kit of claim 30, further comprising said SOCS-3 promoter operatively linked, in a transcriptional unit, to a DNA sequence encoding a protein of interest.

32. The kit of claim 31, wherein the protein of interest is a SOCS-3 protein.

33. The kit of claim 31, wherein said SOCS-3 promoter is operatively linked to a DNA sequence encoding a reporter protein.

34. The kit of claim 33, wherein the encoded reporter protein is a fluorescent or light-emitting protein.

35. The kit of claim 34, wherein the encoded fluorescent or light-emitting protein is a green fluorescent protein, yellow fluorescent protein, blue fluorescent protein, phycobiliprotein, luciferase, or apoaequorin.

36. The kit of claim 31, wherein said polynucleotide further comprises at least one insulator element flanking said transcriptional unit.

37. The kit of claim 36, wherein said at least one insulator element is a chicken β-globin insulator element.

38. The kit of claim 30, further comprising a transfecting agent.

39. The kit of claim 38, wherein the transfecting agent is a liposome, viral vector, transferrin-polylysine enhanced viral vector, retroviral vector, lentiviral vector, or uptake enhancing DNA segment, or a mixture of any of these.

40. The kit of claim 38, wherein the transfecting agent comprises a retroviral vector, adenoviral vector, transferrin-polylysine enhanced adenoviral vector, human immunodeficiency virus vector, lentiviral vector, Moloney murine leukemia virus-derived vector, mumps vector, a DNA segment that facilitates polynucleotide uptake by and release into the cytoplasm of vertebrate cells, or comprises an operative fragment of or mixture of any of these.

41. The kit of claim 38, wherein the transfecting agent comprises an adenovirus vector having endosomal lytic activity, and the polynucleotide is operatively linked to the vector.

42. The kit of claim 38, wherein the transfecting agent comprises a lipid transfecting agent.

* * * * *